(12) United States Patent (10) Patent No.: US 12,688,798 B2
Mali et al. (45) Date of Patent: Jul. 21, 2026

(54) USE OF 3D-PRINTED FREESTANDING STRUCTURES FOR EX VIVO TISSUE

(71) Applicant: THE REGENTS OF THE UNIVERSITY OF CALIFORNIA, Oakland, CA (US)

(72) Inventors: Prashant Mali, La Jolla, CA (US); Udit Parekh, La Jolla, CA (US); Amir Dailamy, La Jolla, CA (US); Xin Lei, La Jolla, CA (US); Michael Hu, La Jolla, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1159 days.

(21) Appl. No.: 17/056,724

(22) PCT Filed: May 21, 2019

(86) PCT No.: PCT/US2019/033409
§ 371 (c)(1),
(2) Date: Nov. 18, 2020

(87) PCT Pub. No.: WO2019/226710
PCT Pub. Date: Nov. 28, 2019

(65) Prior Publication Data
US 2021/0201702 A1     Jul. 1, 2021

Related U.S. Application Data

(60) Provisional application No. 62/674,985, filed on May 22, 2018.

(51) Int. Cl.
| | |
|---|---|
| *G09B 23/30* | (2006.01) |
| *B33Y 80/00* | (2015.01) |
| *C12N 5/00* | (2006.01) |
| *A61M 37/00* | (2006.01) |
| *C08G 18/08* | (2006.01) |
| *C12M 1/32* | (2006.01) |

(52) U.S. Cl.
CPC ............ *G09B 23/306* (2013.01); *B33Y 80/00* (2014.12); *C12N 5/0062* (2013.01); *A61M 2037/003* (2013.01); *C08G 18/14* (2013.01); *C12M 23/12* (2013.01); *C12N 2502/00* (2013.01); *C12N 2513/00* (2013.01); *C12N 2533/30* (2013.01); *C12N 2533/54* (2013.01); *C12N 2533/56* (2013.01); *C12N 2533/74* (2013.01)

(58) Field of Classification Search
None
See application file for complete search history.

(56) References Cited

U.S. PATENT DOCUMENTS

| | | | |
|---|---|---|---|
| 8,318,479 | B2 | 11/2012 | Domansky et al. |
| 2002/0026771 | A1 | 3/2002 | Brown |
| 2018/0110901 | A1* | 4/2018 | Lewis ..................... A61L 27/50 |
| 2019/0367872 | A1* | 12/2019 | Lutolf ................... C12N 5/068 |

OTHER PUBLICATIONS

Mohanty, S. et al., "Fabrication of scalable and structured tissue engineering scaffolds using water dissolvable sacrificial 3D printed moulds" (2015) Materials Science and Engineering C, vol. 55, abstract, p. 2, paragraph 4 (Year: 2015).*

Stoppel, et al, "Transport and Stability of Biological Molecules in Surfactant-Alginate Composite Hydrogels" (2011) Acta Biomaterials, vol. 7. (Year: 2011).*

Chueh, B. et al, "Patterning alginate hydrogels using light-directed release of caged calcium In a microfluidic device" (2010) Biomedical Microdevices, vol. 12, abstract (Year: 2010).*

Chueh, B. et al, "Patterning alginate hydrogels using light-directed release of caged calcium In a microfluidic device" (2010) Biomedical Microdevices, vol. 12, abstract.

International Search Report and Written Opinion dated Aug. 7, 2019, from application No. PCT/US2019/033409.

Lemonnier, et al., "Cell Colonization Ability of a Commercialized Large Porous Alveolar Scaffold" (2017) Applied Bionics and Biomechanics, vol. 2017, figure 1, p. 4, col. 1, paragraph 3.

Mohanty, S. et al., "Fabrication of scalable and structured tissue engineering scaffolds using water dissolvable sacrificial 3D printed moulds" (2015) Materials Science and Engineering C, vol. 55, abstract, p. 2, paragraph 4.

Richards, D. et al., "3D bioprinting for vascularized tissue fabrication" (2017) Annals of Biomedical Engineering, vol. 45.

Stoppel, et al, "Transport and Stability of Biological Molecules in Surfactant-Alginate Composite Hydrogels" (2011) Acta Biomaterials, vol. 7, p. 2, paragraph 2, p. 4, paragraph 5.

(Continued)

*Primary Examiner* — Nghi V Nguyen
(74) *Attorney, Agent, or Firm* — Foley & Lardner LLP

(57) ABSTRACT

The present disclosure provides information on the methodology used in the fabrication of three-dimensional cellularized tissue constructs from free-standing evacuable 3D printed composites and/or scaffolds embedded in an extracellular matrix mimic generated from biocompatible materials. The purposes of using these composite and/or scaffold materials is to generate complex embedded lumens that allow for complete perfusion of the matrix construct by standard cell culture media, thereby allowing for maintenance of large-scale 3D cell cultures in specific geometric forms. The use of biological extracellular matrix materials is to provide essential biological and mechanical signals needed to regulate the behavior of encapsulated cells. Furthermore, the methodology can be adapted such that the lumens generated are capable of being seeded with various endothelial and epithelial cell types as desired, thereby allowing for mimicry of in vivo vasculature, intestinal tracts, and other lumen-containing constructs. This disclosure provides the methodology for generating the tissue constructs.

15 Claims, 25 Drawing Sheets

(56)  References Cited

OTHER PUBLICATIONS

Zhang, et al., "Bioprinting 3D microfibrous scaffolds for engineering endothelialized myocardium and heart-on-a-chip" Biomaterials, vol. 110, Dec. 2016, figure 1.

Khattak, et al., "Pluronic F127 as a Cell Encapsulation Material: Utilization of Membrane-Stabilizing Agents," Tissue Engineering, 2005, vol. 11 No. 5/5, pp. 974-983.

* cited by examiner

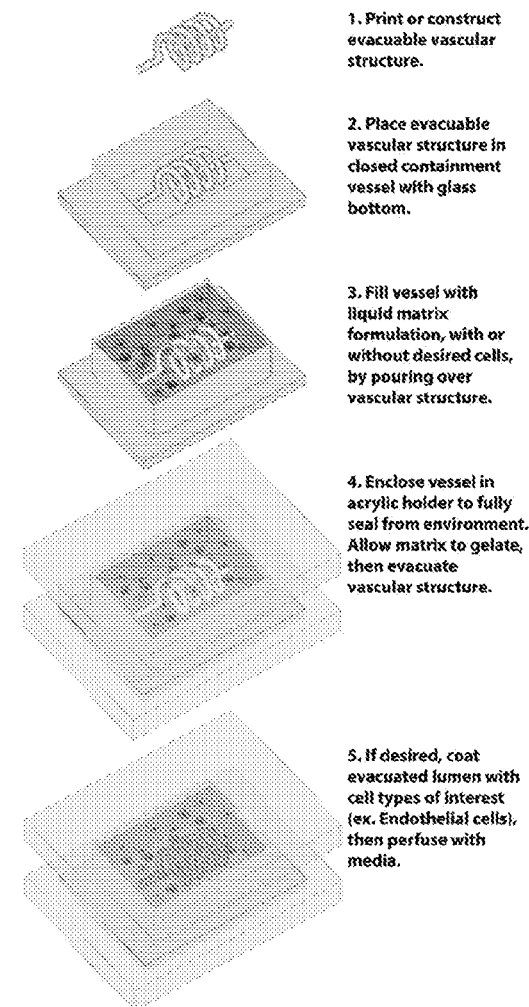

1. Print or construct evacuable vascular structure.

2. Place evacuable vascular structure in closed containment vessel with glass bottom.

3. Fill vessel with liquid matrix formulation, with or without desired cells, by pouring over vascular structure.

4. Enclose vessel in acrylic holder to fully seal from environment. Allow matrix to gelate, then evacuate vascular structure.

5. If desired, coat evacuated lumen with cell types of interest (ex. Endothelial cells), then perfuse with media.

FIG. 1A

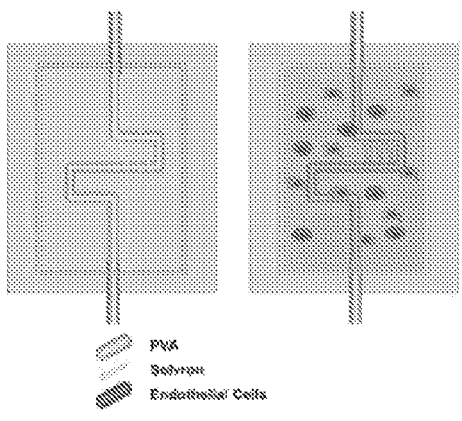

PVA
Solvent
Endothelial Cells

FIG. 1B

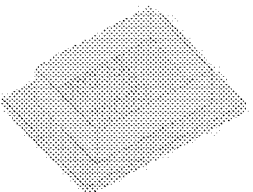
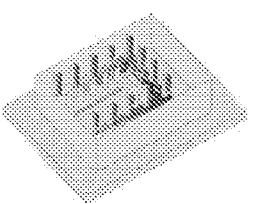
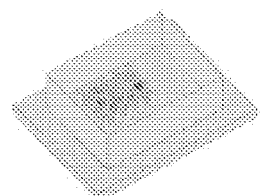

1. Create double-chambered containment vessel with glass bottom. Inner chamber is composed of pillars that entrap fluid via surface tension.

2. Print or weave free-standing scaffold and place within containment vessel

3. Fill inner chamber with liquid matrix, allowing surface tension to hold matrix in.

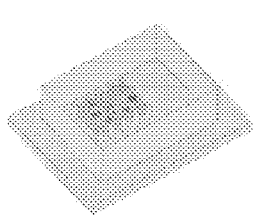
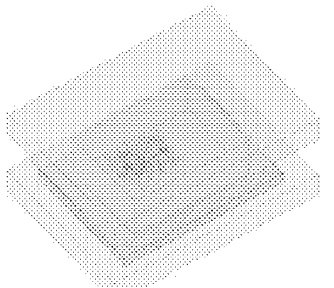

4. Allow matrix to gelate, then evacuate vascular structure.

5. If desired, coat evacuated lumen with cell types of interest (ex. Endothelial cells), then perfuse with media.

FIG. 1C

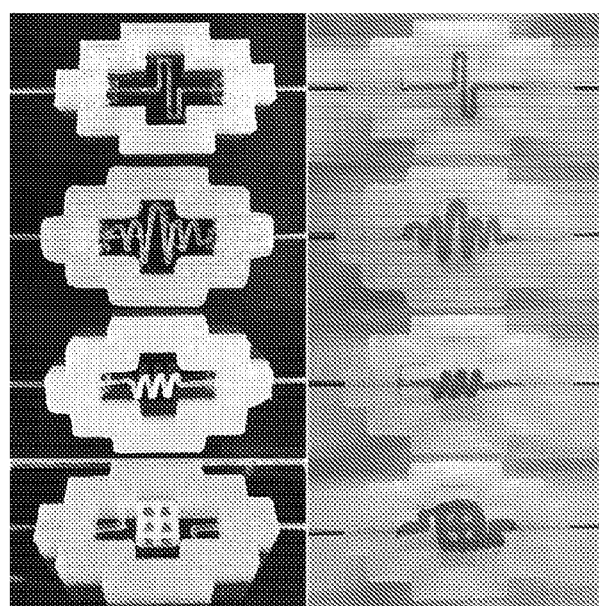

FIG. 2A

Effect of PVA on MDA-MB-231 Growth        Effect of PVA on HUVEC Growth

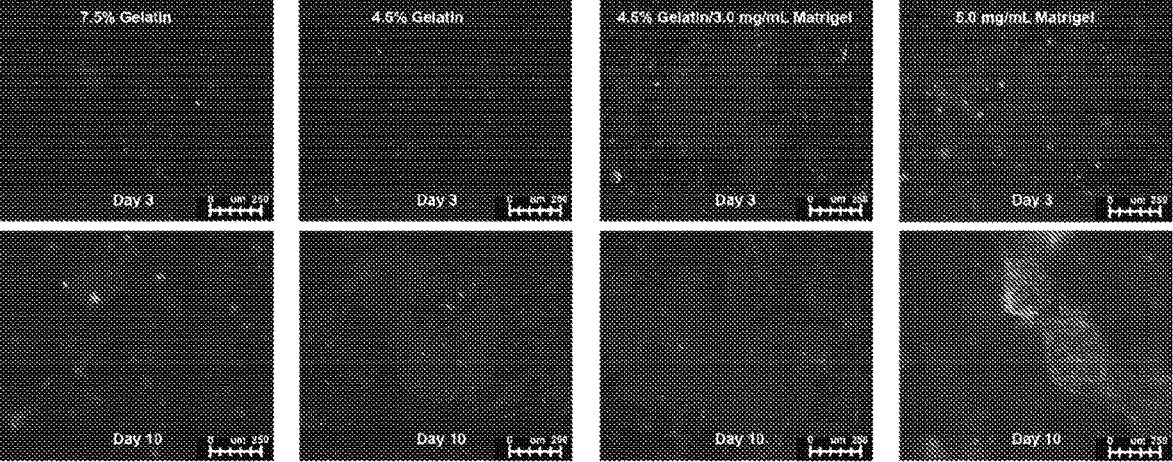
FIG. 7
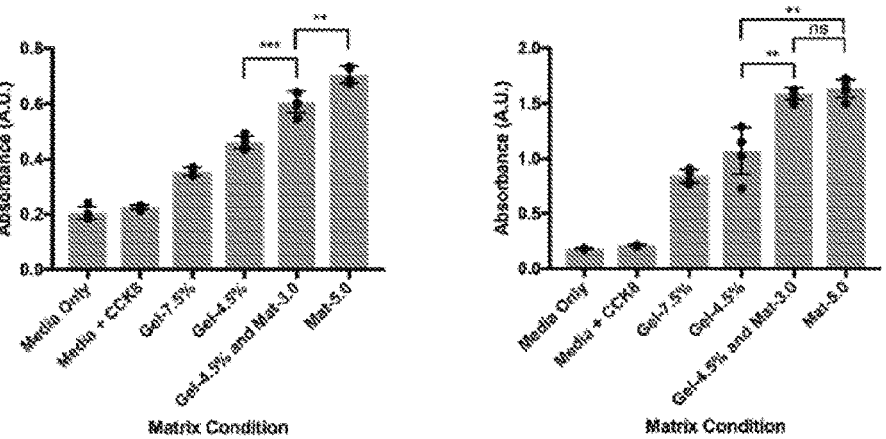
FIGS. 8A – 8B

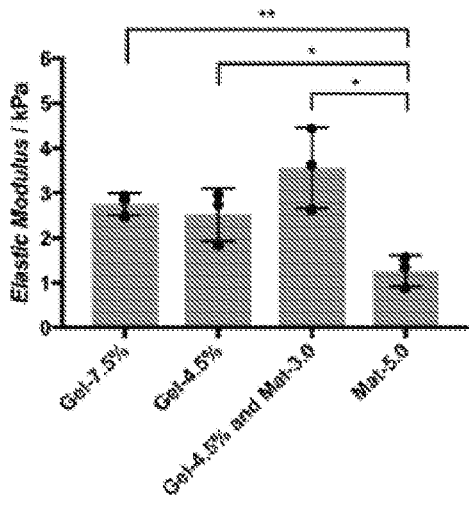
FIG. 8C
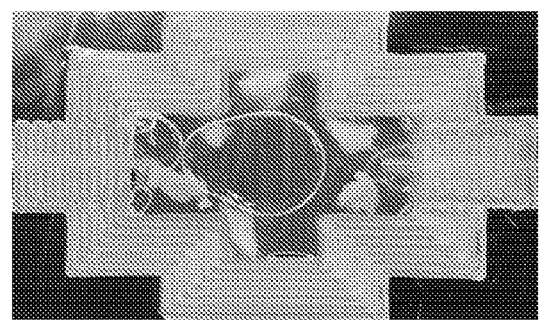 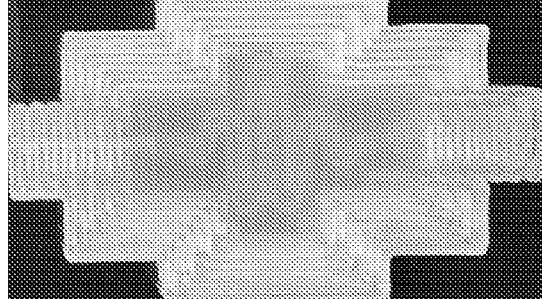
FIGS. 9A – 9B
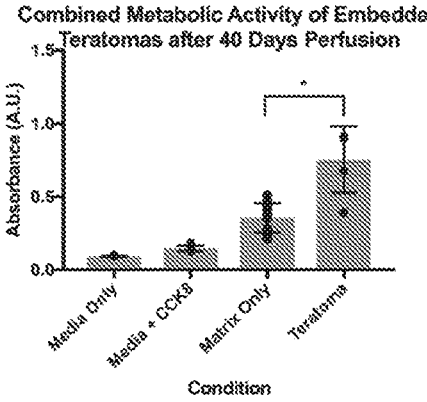
FIG. 10A

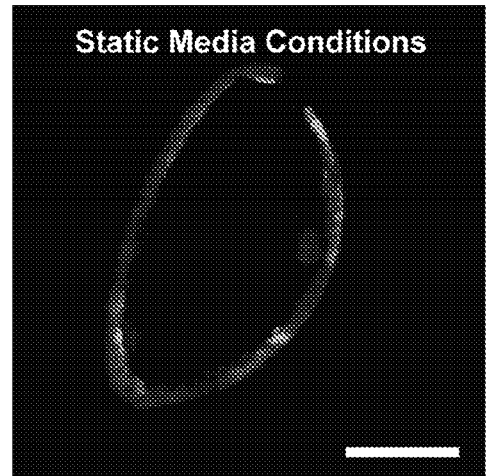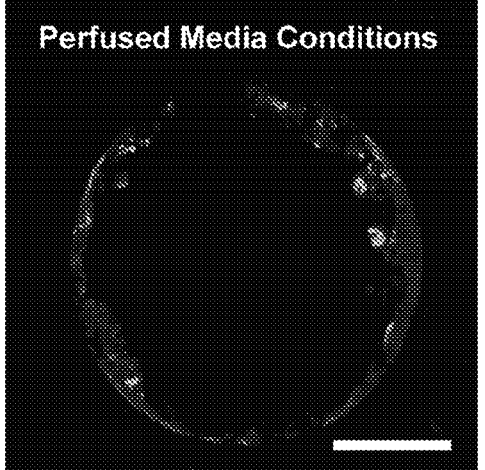
FIG. 16A
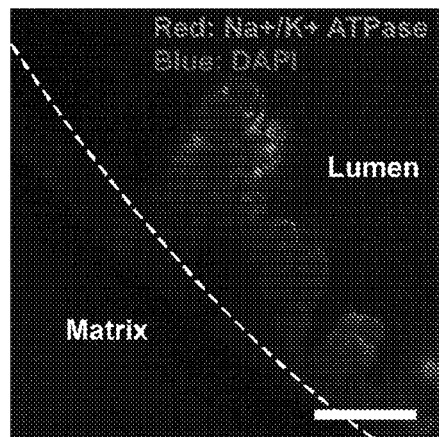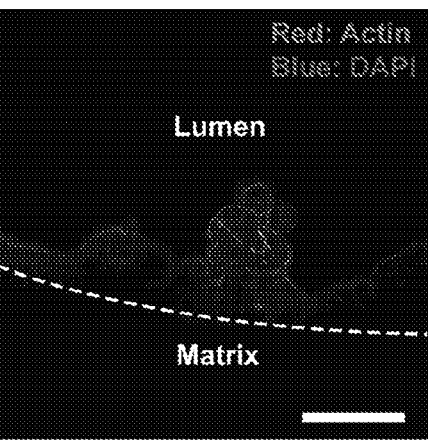
FIG. 16B

Effect of Matrigel Content on hMSC Growth

Effect of Media Composition on HUVEC Growth

Effect of Media composition on MDA-MB-231 Growth

Effect of Media Composition on HUVEC Growth

FIG. 21A

USE OF 3D-PRINTED FREESTANDING STRUCTURES FOR EX VIVO TISSUE

CROSS REFERENCE TO RELATED APPLICATIONS

This application is a national stage application under 35 U.S.C. § 371 of International Application No. PCT/US2019/033409, filed May 21, 2019, which claims priority under 35 U.S.C. § 119(e) to U.S. Provisional Application No. 62/674,985, filed May 22, 2018, the contents each of which are hereby incorporated by reference in their entireties.

STATEMENT OF GOVERNMENT SUPPORT

This invention was made with government support under the Grant Nos. CA222826 and HG009285, awarded by the National Institute for Health (NIH). The government has certain rights in the invention.

BACKGROUND

Presently, drug screening and disease studies are primarily conducted in animal models. Despite containing many of the biologically relevant environmental factors however, these models are often inaccurate representations of the human equivalents, frequently leading to inconsistent results and low translational success. As such, accurate in vitro models of human disease and tissue constructs are extremely desirable. Unfortunately, it is well-established that two-dimensional cell cultures are unable to reproduce the biological complexity of in vivo tissue systems, and most existing three-dimensional models are size-restricted and poorly suited for co-culture due to the unique nutritional requirements of different cell types, as well as the limited diffusion rate of cell nutrients. However, many of these issues can be resolved by generating an easily replicable vascularized three-dimensional tissue model that is able to circumvent the diffusion limitations of increased structural perfusion, the construction of which is described herein.

SUMMARY

The present technology and methods overcome the drawbacks of previously known systems by providing a printed tissue construct comprising, or alternatively consisting essentially of, or yet further consisting of, one or more types of living cells or excised tissue fragments encapsulated in a single material, or blend of materials, serving as an extracellular matrix substitute. The cellularized ex vivo construct includes a hydrogel-based and/or synthetic cell matrix encapsulating a plurality of viable cells or tissue fragments and a hydrogel. The hydrogel can include at least one lumen, or alternatively at least two lumen, or at least three lumen, or at least four lumen, or at least five lumen, or at least six lumen, or at least seven lumen, or at least eight lumen, or at least nine lumen, or at least ten lumen created by loading a free-standing evacuable filament structure in the hydrogel while the hydrogel is in a liquid phase. The free-standing filament structure is dissolved and removed from the hydrogel after the hydrogel is gelated to a solid phase.

The extracellular matrix substituent provided herein contains hollow lumens in one, two, or three-dimensional patterns, allowing it to be perfused with one or more growth media specific to the cell types being sustained. The hollow channels may or may not be lined with endothelial cells or epithelial cells of various types in order to better mimic in vivo vasculature or other organ constructs.

Methods of generating cellularized ex-vivo tissue constructs are also provided. In one method, a plurality of viable cells and/or a plurality of tissue fragments is suspended in a liquid-phase hydrogel to prepare a composite and/or solution. A free-standing evacuable filament structure is then encapsulated within the composite and/or solution, after which the composite and/or solution is gelated to mimic a cellular matrix. Finally, the free-standing filament structure is dissolved and evacuated from the composite and/or gelated solution, thereby creating at least one lumen, or alternatively at least two lumen, or at least three lumen, or at least four lumen, or at least five lumen, or at least six lumen, or at least seven lumen, or at least eight lumen, or at least nine lumen, or at least ten lumen in the cellular matrix.

A method of constructing the tissue model via encapsulation of a free-standing 3D-printed water-soluble poly-vinyl alcohol (PVA) structure in a solution comprising, or alternatively consisting essentially of, or yet further consisting of, a liquid phase and/or pre-gelated extracellular matrix substitute and viable cells or tissue fragments is also provided. Non-limiting examples of water-soluble poly-vinyl alcohol (PVA) structures are provided in Ni et al. (2017) *J Appl Polym Sci.;* 134. Following gelation, the free-standing structure is allowed to partially dissolve in the aqueous environment of the matrix, before being evacuated fully by perfusion.

A method of constructing the tissue model via encapsulation of a free-standing, water-soluble poly-vinyl alcohol thread structure capable of being knitted into specific patterns, in a solution comprising, or alternatively consisting essentially of, or yet further consisting of, a liquid phase and/or pre-gelated extracellular matrix substitute and viable cells or tissue fragments is also provided. Following gelation, the free-standing structure is allowed to partially dissolve in the aqueous environment of the matrix, before being evacuated fully by perfusion.

A method of constructing the tissue model via encapsulation of a free-standing 3D-printed evacuable structure, comprising, or alternatively consisting essentially of, or yet further consisting of a blend of alginate and Pluronics F127, in a solution comprising, or alternatively consisting essentially of, or yet further consisting of a liquid phase and/or pre-gelated extracellular matrix substitute and viable cells or tissue fragments further is provided. Following gelation, the free-standing structure is partially liquefied at about 4° C. and fully dissolved and evacuated using a cold solution of EDTA or an equivalent thereof.

In some embodiments, removing the poly-vinyl alcohol structure comprises complete solvation within the encapsulating matrix, and gradual removal via bathing and incubation in aqueous media. Cell growth media can also be added to the matrix. Any cell growth media added can be used as the solvent to remove the poly-vinyl alcohol. Cell growth media used to perfuse the interior of the lumen or lumens of the construct can contain biological molecules or nanoparticles, including but not limited to growth factors, steroids, carbohydrates, cytotoxins, and amino acids, selected to support the growth and/or maintenance of the cells. Extracellular matrix binding proteins can also be added to the construct, including but not limited to laminin and fibronectin, used to precoat the interior lumen of the construct following evacuation of the free-standing structure, but preceding the addition of any endothelial or epithelial cell types. The construct may also be treated with, or comprise, or alternatively consist essentially of, or yet further consist of pharmacological agents. A method of three-dimensionally coculturing multiple cell types or excised tissue in an environment that mimics extracellular matrix is also provided.

More specifically, and as detailed below, the following embodiments are disclosed herein. In one aspect, provided herein is a method of generating cellularized ex-vivo tissue constructs comprising, or alternatively consisting essentially of, or yet further consisting of:

suspending a plurality of viable cells and/or a plurality of tissue fragments in a liquid-phase hydrogel to prepare a composite and/or solution;

encapsulating a free-standing evacuable filament structure within the composite and/or solution;

gelating the composite and/or solution to mimic a cellular matrix; and dissolving and evacuating the free-standing filament structure to create at least one lumen in the cellular matrix.

In one aspect, the free-standing structure comprises, or alternatively consists essentially of, or yet further consists of single-way channels in a three-dimensional structure selected from helical, sinusoidal, and linear channel. Alternatively, the structure comprises, or alternatively consists essentially of, or yet further consists of multi-way channels in a three-dimensional structure selected from cubical, grid, or a spherical channel. In alternative embodiment, the free-standing evacuable filament structure comprises, or alternatively consists essentially of, or yet further consists of, poly-vinyl alcohol and is three-dimensionally printed, stable in air, and dissolvable in an aqueous solvent. The polyvinyl-alcohol structures can be used in any general singular multi-channel configuration capable of being printed by a 3D printer or an equivalent thereof. In one aspect, the 3D printer is an Ultimaker$^3$ 3D printer. In one aspect, two or more poly-vinyl alcohol structures can be used within the same construct.

In one aspect of the method, threads constructed by poly-vinyl alcohol are knit into an evacuable, free-standing filament structure, wherein the material is stable in air and dissolvable in an aqueous solvent. In a further aspect, polyvinyl alcohol is removed by partial solvation within the encapsulating matrix, followed by attaching the tissue construct to a peristaltic pump and perfusing for about 10 to about 20 minutes, or alternatively for about 11 minutes, or about 12 minutes, or about 13 minutes, or about 14 minutes, or about 15 minutes, or about 16 minutes, or about 17 minutes, or about 18 minutes, or about 19 minutes. In another aspect, the polyvinyl alcohol is removed by partial solvation within the encapsulating matrix, followed by manual perfusion using a pipette. In another aspect, the polyvinyl alcohol is removed by complete solvation within the encapsulating matrix, and gradual removal via bathing and incubation in aqueous media. In a further aspect, any form of cell growth media is used as the solvent to remove the polyvinyl alcohol.

In a further aspect, the method further comprises, or alternatively consists essentially of, or yet further consists of depositing the composite and/or solution around the free-standing evacuable filament structure via micropipette to form a vascular pattern interpenetrating the one or more tissue patterns.

In an alternative aspect, the method further comprises, or alternatively consists essentially of, or yet further consists of removing the polyvinyl alcohol by partial solvation within the encapsulating matrix, followed by attaching the tissue construct to a peristaltic pump and perfusing for about 10 to about 20 minutes, or alternatively for about 11 minutes, or about 12 minutes, or about 13 minutes, or about 14 minutes, or about 15 minutes, or about 16 minutes, or about 17 minutes, or about 18 minutes, or about 19 minutes.

In a yet further aspect, the polyvinyl alcohol is removed by partial solvation within the encapsulating matrix, followed by manual perfusion using a pipette.

In a further aspect, the polyvinyl alcohol is removed by complete solvation within the encapsulating matrix, and gradual removal via bathing and incubation in aqueous media.

In a further aspect, of the method, any form of cell growth media is used as the solvent to remove the polyvinyl alcohol.

In a further aspect, the three-dimensionally printed free-standing structure comprises, or alternatively consists essentially of, or yet further consists of alginate and a pluronic blend, wherein the composite material is dissolvable in an EDTA solution. EDTA commonly chelates metal ions. Materials that are reliant on crosslinking by divalent metal cations can be dissolved in EDTA solution. Two non-limiting examples of common biopolymers that can be dissolved in this manner are alginate (calcium alginate) and pectinate (calcium pectinate).

In a further aspect, the composite material is cross-linked via submersion in a calcium chloride solution at a concentration between about 5 mM to about 250 mM immediately following extrusion.

In a yet further aspect, the method further comprises, or alternatively consists essentially of, or yet further consists of depositing a base matrix layer on a substrate before inserting the alginate-pluronic vasculature structure, wherein top layer of matrix is poured over the vasculature structure to ensure that the evacuable filament is embedded between two matrix layers.

In a yet further aspect, the alginate-pluronic structures are single-way channels comprising, or alternatively consisting essentially of, or yet further consisting of sinusoidal and linear channels or are multi-way channels comprising, or alternatively consisting essentially of, or yet further consisting of cubical and grid-shaped channels. Alternatively, the alginate-pluronic structures are any general singular multi-channel configuration capable of being generated by an extrusion printer.

In a yet further aspect of this method, the alginate-pluronic structure is removed by a method comprising, or alternatively consisting essentially of, or yet further consisting of incubation in about 2 to about 6 degrees Celsius, or alternatively about 4 degrees Celsius to liquify a pluronics component, followed by evacuation with cold media containing EDTA by micropipettes.

In a further aspect, any two or more of the methods are used in combination.

The methods as disclosed herein make a composite and/or hydrogel. In one aspect, the composite and/or hydrogel designed to mimic the extracellular matrix comprises, or alternatively consists essentially of, or yet further consists of at least one, or alternatively at least two, or at least three, or at least four, or at least five, or at least six, or at least seven, or at least eight, or at least nine of Matrigel, fibrin, gelatin, bovine collagen, porcine collagen, rat-tail collagen, gelatin methacrylate, alginate, decellularized extracellular matrix, or polyethylene glycol, alone or in combination with each other. In one aspect, the method is performed to provide combination of materials comprises, or alternatively consists essentially of, or yet further consists of about 1.5 mg/mL gelatin, about 4.0 mg/mL matrigel, and about 10 mg/mL fibrin. The material prepared by this method also is disclosed herein.

The method can be modified by the introduction of one or more viable human or non-human cell types encapsulated within the construct. In one aspect, combinations of human and non-human cell types are encapsulated within the construct. The cell-composite and/or hydrogel constructs prepared by these methods also are disclosed herein.

In one aspect, the method further comprises or alternatively consists essentially of, or yet further consists of perfusing the interior lumen or lumens of the construct with perfused with cell growth media. In another aspect, the methods are modified to provide two or more distinct interior lumens of the construct can be perfused with distinct types of cell growth media. In a further aspect, the methods are modified such that one or more viable human or non-human endothelial or epithelial cell types are used to coat the interior lumen of the construct following evacuation of the free-standing structure. In a further aspect, the methods are modified such that one or more different viable human or non-human endothelial or epithelial cell types are used in distinct lumens of the construct following evacuation of the free-standing structure.

In a further aspect of the methods, the cell growth medium or media used to perfuse the interior of the lumen or lumens of the construct contain biological molecules or nanoparticles, including but not limited to growth factors, steroids, carbohydrates, cytotoxins, and amino acids. Non-limiting examples of extracellular matrix binding proteins, include, but are not limited to laminin and fibronectin, are used to precoat the interior lumen of the construct following evacuation of the free-standing structure, but preceding the addition of endothelial or epithelial cell types.

In a further aspect of the methods, the fragments of excised tissue are encapsulated within the body of the matrix construct.

The methods can further add to the compositions a pharmacological agent, and/or generate the constructs in replicate and treat with pharmacological agents, anti-cancer agents and drugs. Non-limiting examples of pharmacological agents include: pharmaceuticals, such as Paclitaxel and Veliparib; pharmaceuticals conjugated with nanoparticles, such as Abraxene; small biomolecules, such as Sphingosine-1-Phosphate or Phorbol 12-myristate 13-acetate; growth Factors, such as fibroblast growth factor, or human epidermal growth factor; other molecules, such as heparin, or cholera toxin.

The constructs as made by the methods disclosed herein have various uses. For example, they can be used to generate an in vitro model of a tumor directly by encapsulation and perfusing of primary tumor cells or a carcinoma cell line within the matrix. Alternatively, the methods are useful to generate an ex vivo model of a tumor and perfused sustenance of excised tumor fragments within the matrix. They also are useful to generate an in vitro model of highly dense vasculature by seeding of human or animal endothelial cells within one or more lumens, encapsulation of human or animal endothelial cells within the matrix, and the addition of pro-angiogenic biomolecules or a gradient of pro-angiogenic biomolecules. Non-limiting examples of pro-angiogenic biomolecules are described in Huang et al. (2004) *World journal of gastroenterology,* 10(4), 463-470. In a further aspect, they are useful to generate an in vitro model of a gut by seeding and sustenance of primary intestinal epithelial cells or an intestinal epithelial cell line within one or more lumens. They also can be used to generate any additional organoid models via seeding and sustenance of primary somatic cells, cell lines, or primary stem cells either within the lumen or within the matrix body.

In a further aspect, the constructs are used as a three-dimensional structure that allows for coculturing multiple cell types or excised tissue in an environment that mimics extracellular matrix. In this aspect, the construct made by these methods generate organoid-like structures from excised tissue or primary stem cells in specific geometries.

To use the constructs, one of skill in the art can subject the endothelial or epithelial cells within the constructs to specific flow rates.

In a specific aspect, this disclosure provides a method of formulating a construct comprising, or alternatively consisting essentially of, or yet further consisting of, adding MDA-MB-231 cells in a stroma, further comprising, or alternatively consisting essentially of, or yet further consisting of post-evacuation seeding of endothelial cells, and long-term perfusion to generate a tumor organoid using the methods disclosed above.

Further provided herein is a cellularized ex-vivo tissue construct comprising, or alternatively consisting essentially of, or yet further consisting of a synthetic and/or hydrogel-based cell matrix comprising, or alternatively consisting essentially of, or yet further consisting of a plurality of viable cells or tissue fragments and a hydrogel, wherein the hydrogel comprises, or alternatively consists essentially of, or yet further consists of at least one lumen, or alternatively at least two lumen, or at least three lumen, or at least four lumen, or at least five lumen, or at least six lumen, or at least seven lumen, or at least eight lumen, or at least nine lumen, or at least ten lumen created by loading a free standing evacuable filament structure in the hydrogel while the hydrogel is in a liquid phase and dissolving and removing the free standing filament structure from the hydrogel after the hydrogel is gelated to a solid phase. In one aspect, the free-standing evacuable filament structure comprises, or alternatively consists essentially of, or yet further consists of poly-vinyl alcohol and is three-dimensionally printed, stable in air, and dissolvable in an aqueous solvent. The filament structure can comprise, or alternatively consist essentially of, or yet further consist of single-way channels in a three-dimensional structure selected from helical, sinusoidal, and linear channel, or alternatively, multi-way channels in a three-dimensional structure selected from cubical, grid, or a spherical channel. In a further aspect, the polyvinyl-alcohol filament structures can be of any general singular multi-channel configuration capable of being printed by a 3D printer or an equivalent thereof. In one aspect, the 3D printer is an Ultimaker³ 3D printer.

The tissue construct can comprise, or alternatively consist essentially of, or yet further consist of two or more poly-vinyl alcohol structures within the same construct. The constructs can be made by methods comprising, or alternatively consisting essentially of, or yet further consisting of depositing the composite and/or solution around the free-standing evacuable filament structure via micropipette to form a vascular pattern interpenetrating the one or more tissue patterns.

The polyvinyl alcohol can be removed by another appropriate method, e.g., by partial solvation within the encapsulating matrix, followed by attaching the tissue construct to a peristaltic pump and perfusing for about 10 to about 20 minutes, or alternatively for about 11 minutes, or about 12 minutes, or about 13 minutes, or about 14 minutes, or about 15 minutes, or about 16 minutes, or about 17 minutes, or about 18 minutes, or about 19 minutes. Alternatively, it can be removed by partial solvation within the encapsulating matrix, followed by manual perfusion using a pipette. In a yet further aspect, the PVA is removed by complete solvation within the encapsulating matrix, and gradual removal via bathing and incubation in aqueous media. Yet further the PVA can be removed by use of any form of cell growth media as the solvent.

In one aspect, the three-dimensionally printed free-standing structure comprises alginate and pluronic blend, wherein the composite material is dissolvable in an EDTA solvent. The composite material can be cross-linked via submersion in a calcium chloride solution at a concentration between about 5 to about 250 mM immediately following extrusion. Alternatively, the composite can be applied by depositing a base matrix layer on a substrate before inserting the alginate-pluronic vasculature structure, wherein top layer of matrix is poured over the vasculature structure to ensure that the evacuable filament is embedded between two matrix layers. In one aspect, the composite refers to an alginate/pluronics blend.

The alginate-pluronic structures can be of any form or three-dimensional structures, e.g., single-way channels comprising, or alternatively consisting essentially of, or yet further consisting of sinusoidal and linear channels, multi-way channels comprising, or alternatively consisting essentially of, or yet further consisting of cubical and grid-shaped channels, or singular multi-channel configuration capable of being generated by an extrusion printer.

The disclosure also provides constructs made by the methods disclosed herein wherein the alginate-pluronic structure (e.g., Alginate/Pluronics F127 blend) are removed by incubation at a temperature capable of liquifying a pluronics component, followed by evacuation with cold media containing EDTA by micropipettes or perfusion by peristaltic pump. In one aspect, the desired temperature for liquification of the pluronics component is from about 2 to about 8 degrees Celsius, or alternatively from about 3 to about 6 degrees Celsius, or alternatively from about 4 to about 5 degrees Celsius, or alternatively about 4 degrees Celsius, or about 7 degrees Celsius. In addition, the constructs disclosed herein are made by threads constructed by poly-vinyl alcohol knit into an evacuable, free-standing filament structure, wherein the composite material is stable in air and dissolvable in an aqueous solvent. The constructs disclosed herein can be made by removing the polyvinyl alcohol comprises, or alternatively consists essentially of, or yet further consists of partial solvation within the encapsulating matrix, followed by attaching the tissue construct to a peristaltic pump and perfusing for about 5 to about 30, or about 5 to about 20, or about 10 to about 20 minutes, or about 15 minutes. Alternatively, the polyvinyl alcohol is removed by partial solvation within the encapsulating matrix, followed by manual perfusion using a pipette, or by complete solvation within the encapsulating matrix, and gradual removal via bathing and incubation in aqueous media. The media can be any form of cell growth media.

As noted herein, the composites and/or hydrogel can be designed to mimic the extracellular matrix comprising, or alternatively consisting essentially of, or yet further consisting of at least one or alternatively at least two, or at least three, or at least four, or at least five, or at least six, or at least seven, or at least eight, or at least nine of Matrigel, fibrin, gelatin, bovine collagen, porcine collagen, rat-tail collagen, gelatin methacrylate, alginate, decellularized extracellular matrix, or polyethylene glycol, alone or in combination with each other. In one particular aspect, the combination of materials comprises, or alternatively consists essentially of, or yet further consists of about from about 1.0 to about 15 mg/mL fibrin, or about 1.0 to about 10 mg/mL, or about 2.0 mg/mL to about 10 mg/mL, or about 3.0 to about 7.0 mg/mL about 1.5 mg/mL gelatin, or about 2.0 mg/mL or about 3.0 mg/mL, or about 4.0 mg/mL matrigel, or about 5.0 mg/mL, or about 6.0 mg/mL or about 7.0 mg/mL or about 8.0 mg/mL or about 9.0 mg/mL, or about 10 mg/mL fibrin.

The composites and/or hydrogels can further comprise, or alternatively consist essentially of, or yet further consist of one or more of viable human or non-human cell types or combinations thereof to form a solution. The cells can be from established commercially available cell lines or fresh and isolated from a tissue biopsy.

Also provided herein is a construct wherein the interior lumen or lumens of the construct is perfused with cell growth media, or wherein two or more distinct interior lumens of the construct can be perfused with distinct types of cell growth media, or yet further wherein one or more viable human or non-human endothelial or epithelial cell types are used to coat the interior lumen of the construct following evacuation of the free-standing structure. The cell growth medium or media used to perfuse the interior of the lumen or lumens of the construct can contain biological molecules or nanoparticles, including but not limited to growth factors, steroids, carbohydrates, cytotoxins, and amino acids. Non-limiting examples of extracellular matrix binding proteins, include but not limited to laminin and fibronectin, are used to precoat the interior lumen of the construct following evacuation of the free-standing structure, but preceding the addition of endothelial or epithelial cell types.

In another aspect, one or more different viable human or non-human endothelial or epithelial cell types are used in distinct lumens of the construct following evacuation of the free-standing structure.

The constructs can further contain fragments of excised tissue are encapsulated within the body of the matrix construct and/or pharmacological agents.

BRIEF DESCRIPTION OF THE DRAWINGS

FIGS. 1A-1C: (FIG. 1A) Schematic describing the main steps in the construction of a perfusable tissue construct. A free-standing scaffold is generated independently of the construct and is placed within an enclosed container. An extracellular matrix substitute solution is subsequently deposited over the construct, and is allowed to transition to gel phase. The construct is then sealed, and the scaffold is dissolved and evacuated. The resulting lumen is perfused with cell growth media, and can be seeded with a desired cell type by the user. (FIG. 1B) Schematic describing a modification to the construction of a perfusable tissue construct to produce vascular lumens of greater density. All steps are identical to those described in FIG. 1A, but the free-standing scaffold is modified via wrapping of water-soluble polyvinyl alcohol-based threads that are able to be evacuated along with the main scaffold. (FIG. 1C) Schematic describing the main steps in the construction of a perfusable tissue construct capable of interstitial flow. Methodology is identical to that described in FIG. 1A, but encapsulation, evacuation, and perfusion take place in a double-chambered container, with the matrix only being added to the inner container.

FIGS. 2A-2D: (FIG. 2A) Multiple examples of scaffold patterns generated via the Ultimaker$^3$ desktop 3D printer using poly-vinyl alcohol, along with the results after being encapsulated in a clear matrix composed of a blend of gelatin and fibrin, evacuated, and perfused with red liquid. Distinct patterns shown are square wave, sinusoidal, spiral, and grid. (FIG. 2B) An example of a matrix of gelatin and fibrin containing lumens generated via evacuation of two distinct scaffold patterns in combination, both generated by the Ultimaker³ desktop 3D printer using poly-vinyl alcohol. The first scaffold pattern was a spiral, and is perfused with a red liquid. The second scaffold pattern was a linear channel, and is perfused with a green liquid. (FIG. 2C) An example of a complex free-standing scaffold pattern in the form of a high-density 3D grid, generated by the Ultimaker³ desktop 3D printer using poly-vinyl alcohol. (FIG. 2D) An example of a scaffold pattern formed by wrapping evacuable poly-vinyl alcohol threads (Solvron, Nitivy Co.) around a main, free-standing scaffold generated by the Ultimaker³ desktop 3D printer using poly-vinyl alcohol.

(FIG. 5A) Quantitative experimental results in which MDA-MB-231 breast carcinoma cells (left) and human umbilical vein endothelial cells (right) were cultured in growth media with or without the presence of poly-vinyl alcohol (1 g/mL). Cell growth was measured via absorbance levels generated by the CCK8 reagent (Dojindo). (FIG. 5B) Qualitative experimental results in which MDA-MB-231 breast carcinoma cells and human umbilical vein endothelial cells were cultured in growth media with or without the presence of poly-vinyl alcohol (about 1 g/mL).

FIG. 7: Qualitative experimental results in which MDA-MB-231 breast carcinoma cells were grown in 3D culture over 10 days following encapsulation in matrices of different compositions. All matrices contained about 10 mg/mL fibrin, along with one of the following: about 7.5% gelatin, about 4.5% gelatin, about 4.5% gelatin and about 3 mg/mL Matrigel, about 5 mg/mL Matrigel. Cells were GFP-labeled, and images were obtained using a Widefield Microscope.

FIGS. 8A-8C: Quantitative experimental results in which (FIG. 8A) MCF7 breast carcinoma cells and (FIG. 8B) MDA-MB-231 breast carcinoma cells were grown in 3D culture over 10 days following encapsulation in matrices of different compositions. All matrices contained about 10 mg/mL fibrin, along with one of the following: about 7.5% gelatin, about 4.5% gelatin, about 4.5% gelatin and about 3 mg/mL Matrigel, about 5 mg/mL Matrigel. Cell growth was measured via absorbance levels generated by the CCK8 reagent (Dojindo). (FIG. 8C) Quantitative results indicating the elastic moduli of experimental matrices of various compositions. All matrices contained 10 mg/mL fibrin, along with one of the following: 7.5% gelatin, 4.5% gelatin, 4.5% gelatin and 3 mg/mL Matrigel, 5 mg/mL Matrigel. Elastic modulus measurements were obtained via atomic-force microscopy.

FIGS. 9A-9B: (FIG. 9A) An example of a 3D tissue construct formulated using a matrix of about 1.5% gelatin, about 4 mg/mL Matrigel, and about 10 mg/mL fibrin with evacuated vascular channels in a sinusoidal poly-vinyl alcohol pattern and embedded tumor fragments excised from a mouse-grown MDA-MB-231 breast carcinoma tumor. (FIG. 9B) An example of a 3D tissue construct formulated using a matrix of about 5 mg/mL Matrigel and about 10 mg/mL fibrin with evacuated vascular channels in a sinusoidal poly-vinyl alcohol pattern with encapsulated MDA-MB-231 breast carcinoma cells.

FIGS. 10A-10D: (FIG. 10A) Quantitative experimental results in which fragments of teratomas generated from human induced pluripotent stem cells in mice were embedded in perfused matrix constructs of about 5 mg/mL matrigel and about 10 mg/mL fibrin. Matrices also encapsulated human mesenchymal stem cells (hMSCs) and human umbilical vein endothelial cells (HUVECs). Teratoma fragments were perfused within the matrix for 40 days, after which they were excised and had metabolic activity compared to matrix fragments containing only hMSCs and HUVECs. Metabolic activity was measured via absorbance levels generated by the CCK8 reagent (Dojindo). (FIG. 10B) Quantitative experimental results in which fragments of tumors generated from GFP-labeled MDA-MB-231 cells in mice were embedded in either matrix constructs under static media conditions, or perfused matrix constructs. All matrix constructs had compositions of about 1.5 mg/mL gelatin, about 4.0 mg/mL matrigel, and about 10 mg/mL fibrin. Matrices also encapsulated human mesenchymal stem cells (hMSCs) and human umbilical vein endothelial cells (HU-VECs). Tumor fragments were allowed to grow in either static matrices (with daily media changes) or perfused matrices for 20 days, after which they were excised and had metabolic activity compared measured via absorbance levels generated by the CCK8 reagent (Dojindo). Metabolic quantifications were normalized to the mass of the tumor fragment that generated them. (FIG. 10C) Qualitative experimental results from the experiment described in FIG. 10B. Prior to extraction, tumor fragments were imaged from within the perfused matrix construct via Confocal Microscopy at 490 nm. Scale bar represents 300 μm. Dashed outline represents the location of the vascular channel, which is out of the visible plane. (FIG. 10D) Qualitative experimental results from the experiment described in FIG. 10B. Following extraction, tumors were embedded in Optimal Cutting Temperature (OCT) compound, cryosectioned, and imaged via Widefield Microscopy at 490 nm as well as under brightfield settings. Magnitude of green fluorescence correlates to proportion of still-living tissue. Scalebars represent 500 μm.

(FIG. 11A) An example of a channel produced via evacuation of a free-standing spiral-shaped PVA scaffold, and seeded with mCherry-labeled human umbilical vein endothelial cells. (FIG. 11B) An example of a channel produced via evacuation of a free-standing linear PVA scaffold, and seeded with mCherry-labeled human umbilical vein endothelial cells. The images show the longitudinal section (left) and the cross-section (right) of an evacuated vascular channel. Scale bars represent 400 μm. (FIG. 11C) Immunostains of human umbilical vein endothelial cells for CD34 (left) and VE-Cadherin (right) following seeding within a perfused construct and perfusion over a period of 10 days. Scale bars represent 100 μm. (FIG. 11D)

An example of multi-channel structure produced via evacuation of a free-standing sinusoid-shaped PVA scaffold threaded with poly-vinyl alcohol-based threads (Solvron), and seeded with mCherry-labeled human umbilical vein endothelial cells. Scale bar represents 1 mm.

Figure 12:
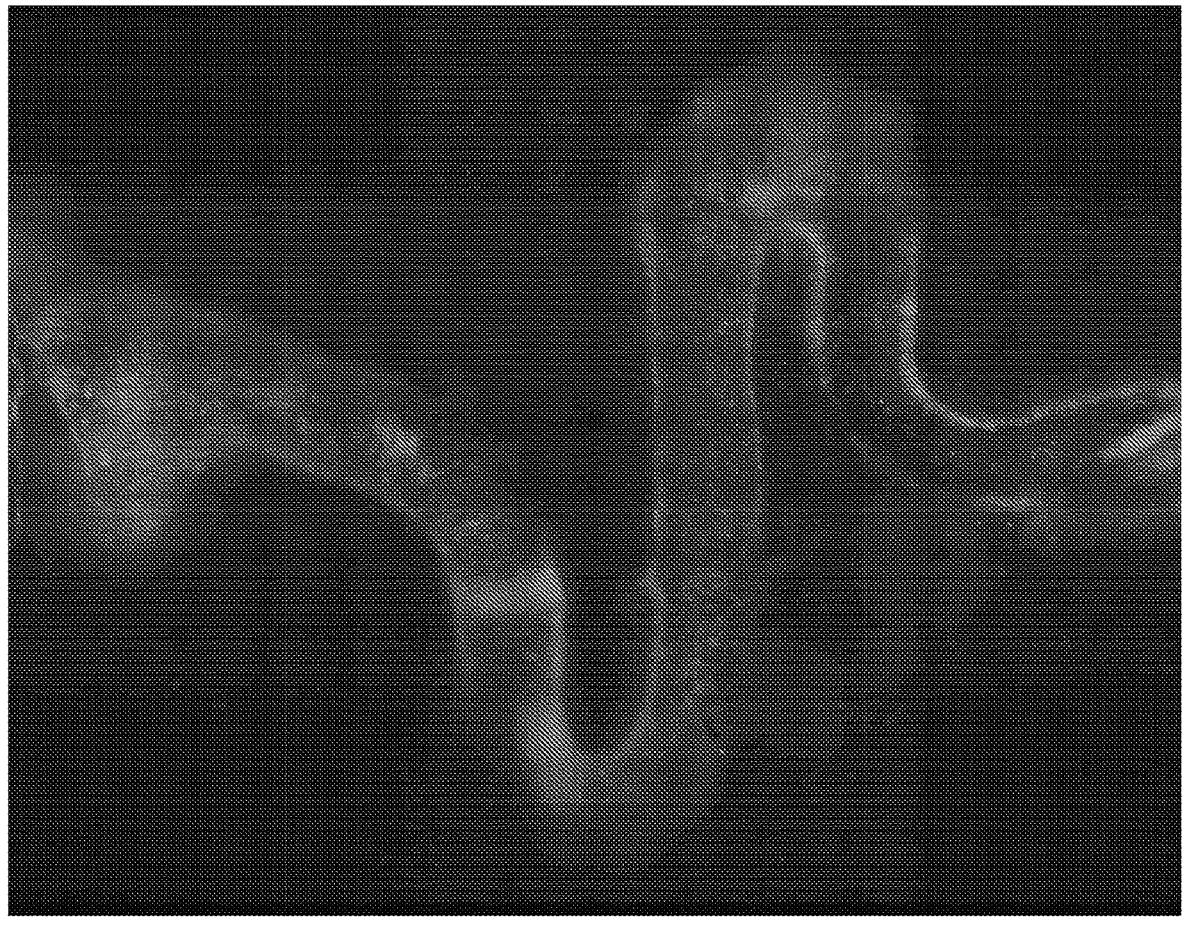

FIG. 12: An example of a channel produced via evacuation of a free-standing sinusoidal scaffold produced via extrusion of about 0.5% alginate and about 40% Pluronics F127, and seeded with mCherry-labeled human umbilical vein endothelial cells.

Figure 13:

FIG. 13: An example of a channel produced via evacuation of a free-standing sinusoidally-shaped PVA scaffold, and seeded with mCherry-labeled human umbilical vein endothelial cells. The surrounding matrix also encapsulated GFP-labeled MDA-MB-231 cells.

Figure 14:
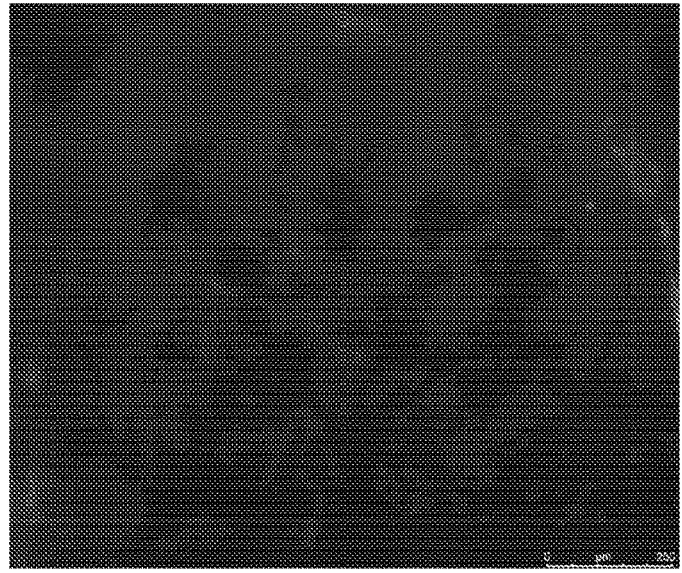

FIG. 14: An example of a channel produced via evacuation of a free-standing sinusoidal scaffold produced via extrusion of about 0.5% alginate and about 40% Pluronics F127, and seeded with mCherry-labeled human umbilical vein endothelial cells that later underwent angiogenic sprouting to expand the perfused volume.

Figure 15:
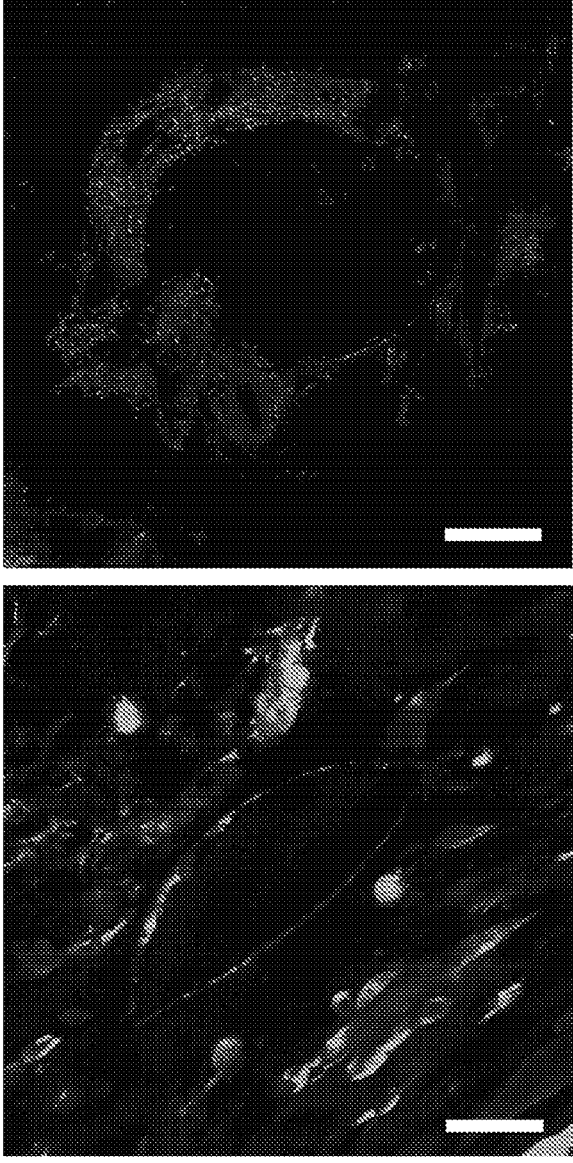

FIG. 15: Examples of tumor models grown in vitro using perfused vascularized constructs generated via evacuation of PVA. Green cells represent GFP-labeled MDA-MB-231 cells, while red cells represent mCherry-labeled human umbilical vein endothelial cells. Scale bars represent 400 μm (left) and 200 μm (right).

FIGS. 16A-16B: (FIG. 16A) Examples of perfused gut models generated via evacuation of PVA followed by seeding with Caco-2 gut epithelial cells. Caco-2 cells seeded within the channel but cultured under static conditions (no flow) are shown to the left, while Caco-2 cells cultured under perfused media conditions are shown to the right. Scale bars represent 200 um (left) and 400 um (right). (FIG. 16B) Immunostains of Caco-2 cells for $Na^+/K^+$ ATPase (left) and Actin (right) following seeding within a perfused construct and perfusion over a period of 12 days. Scale bars represent 50 μm.

Figure 17A:
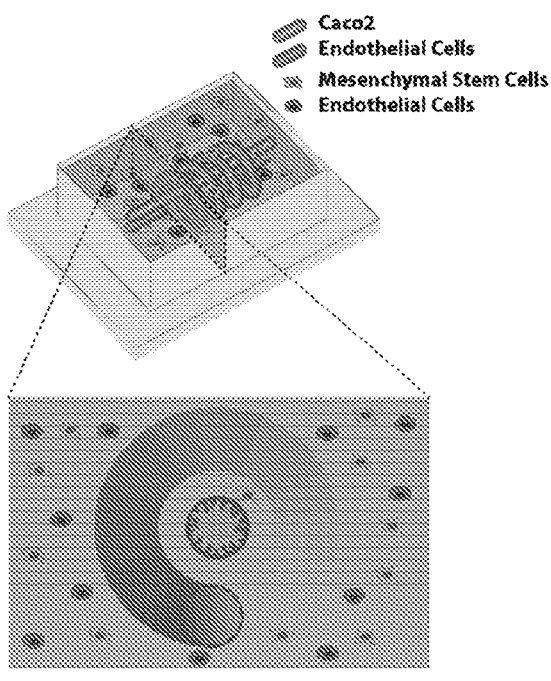
Figure 17B:
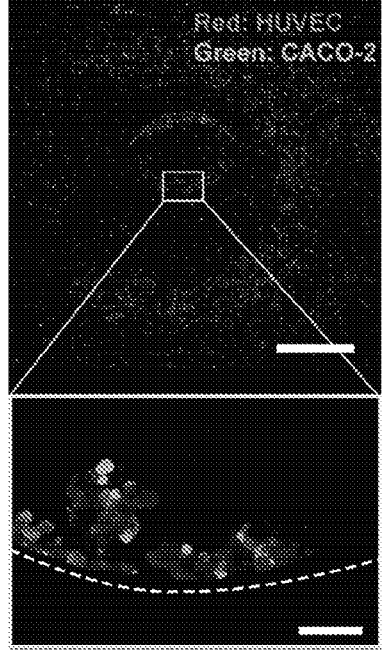

FIGS. 17A-17B: (FIG. 17A) A schematic of the design of a hybrid organoid system comprising, a perfused gut model surrounded by a vascular endothelial network. The gut was designed as a linear channel seeded with GFP-labeled Caco-2 cells, while the endothelial network was constructed as a spiral channel formed from evacuated PVA, and seeded with human umbilical vein endothelial cells. (FIG. 17B) Confocal images of an actual hybrid organoid system designed exactly as described in FIG. 17A. The images were taken after 18 days, and show a cross-section of the perfused construct. The central channel consists of seeded Caco-2 cells, while the outer spiral is covered by human umbilical vein endothelial cells. A close-up of the central channel shows that the Caco-2 cells exhibit villi-like protrusions. Scale bars represent 1 mm and 100 μm.

Figure 18A:
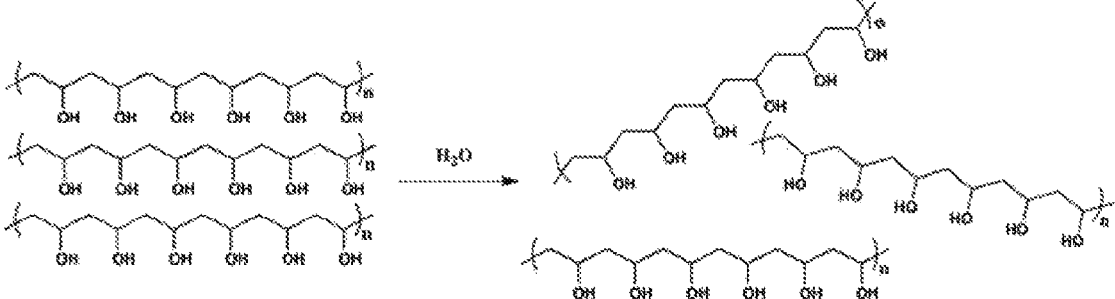
Figure 18B:
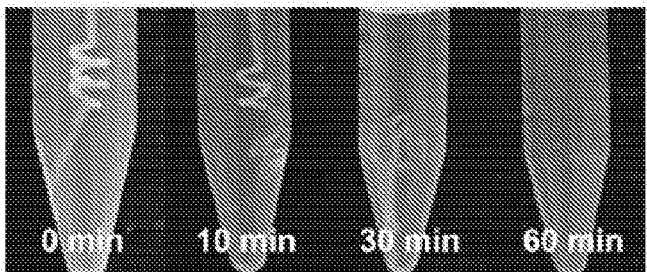
Figure 18C:
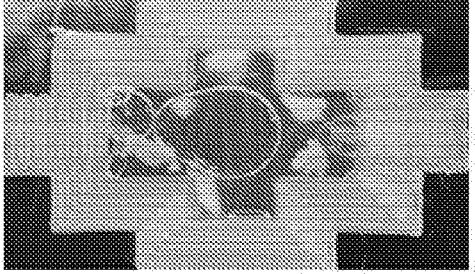
Figure 18D:
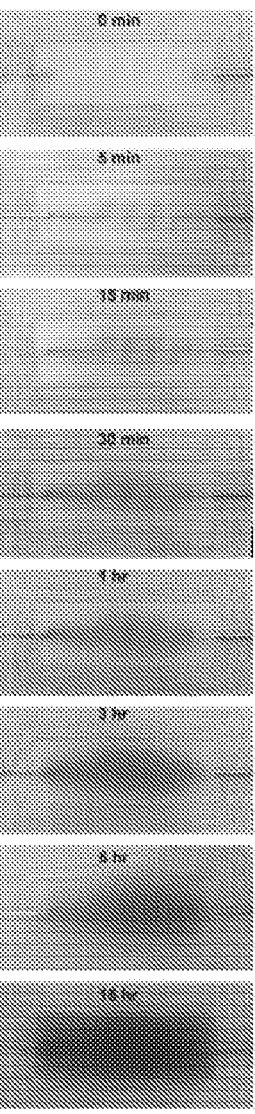

FIGS. 18A-18D: As shown in FIG. 18A, the Schematic—PVA Chemistry outlines the chemistry associated with poly (vinyl alcohol) that allows for it to be easily dissolved in water. As shown in FIG. 18B, in the first series of studies the viability of using PVA as a sacrificial vascular scaffold was assessed. PVA was confirmed to completely dissolve in media within a 1-hour time-frame, likely attributed to its water-soluble chemistry. Depicted in FIG. 18C, the image "Prototype—Print-15gel-4mat-Tumors_top_02418" shows a completed tissue construct designed to sustain embedded MDA-MB-231 tumor fragments (excised from mice) over time. As illustrated in FIG. 18D, the image, "Experimental Data—Dye_Perfusion_bottom_012308.png" shows an example of nutrient diffusion through the vascularized tissue construct via permeation patterns of dye over an 18-hour period.

Figure 19A:
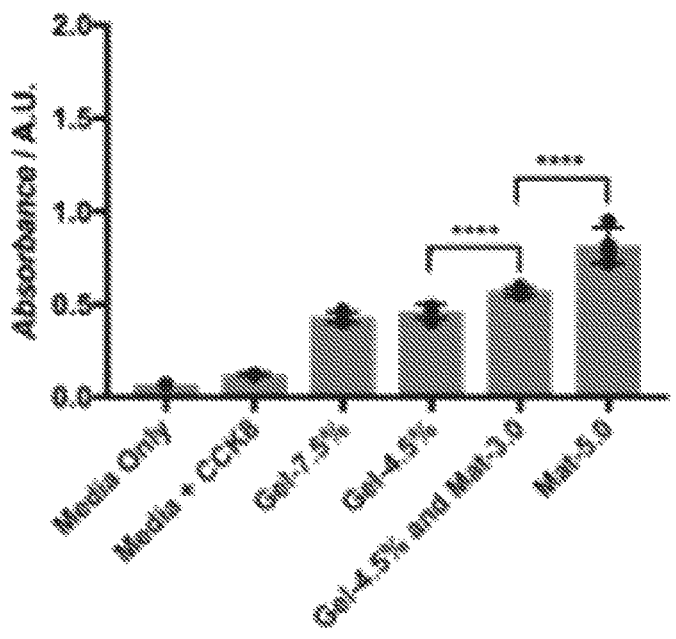
Figure 19B:
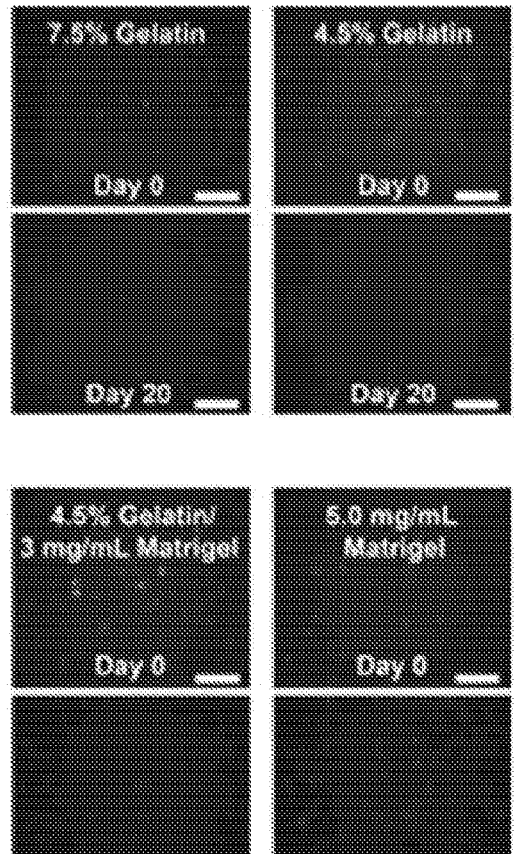

FIGS. 19A-19B: As shown in FIG. 19A and FIG. 19B, an identical experiment was conducted with hMSCs to assess the effect on the stromal cells, with the duration increased to 20 days to account for a slower rate of growth. Both quantitative and qualitative results mirrored those of the breast cancer epithelial cells.

FIGS. 20A-20D: Qualitative results (FIG. 20A and FIG. 20B) and quantitative results (FIG. 20C and FIG. 20D) indicate that a 50/50 mixture of EGM-2 and DMEM supplemented with 20% FBS and 4 mM L-glutamine maximized growth of MDA-MB-231 cells while producing no significant effect on the growth of HUVECs compared to controls in EGM-2 only.

Figure 21A:
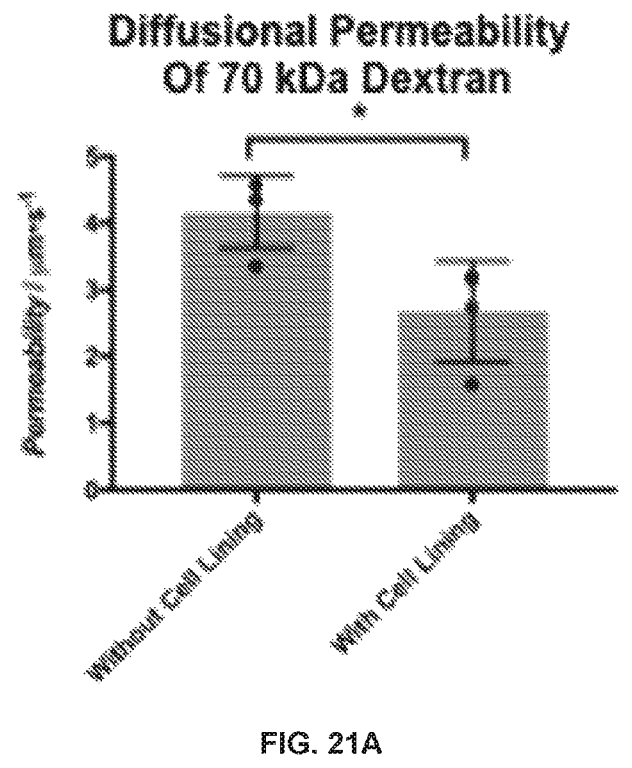

FIG. 21A depicts vascular permeability measurements, wherein FITC-labeled 70 kDa dextran was flowed through channels either with or without a coating of HUVECs at a rate of 20 μL/min, and allowed to diffuse over 3 minutes to obtain an initial fluorescence measure. This rate was then reduced to 5 μL/min for the next 30 minutes, with fluorescent images taken every 5 minutes.

Figure 21B:
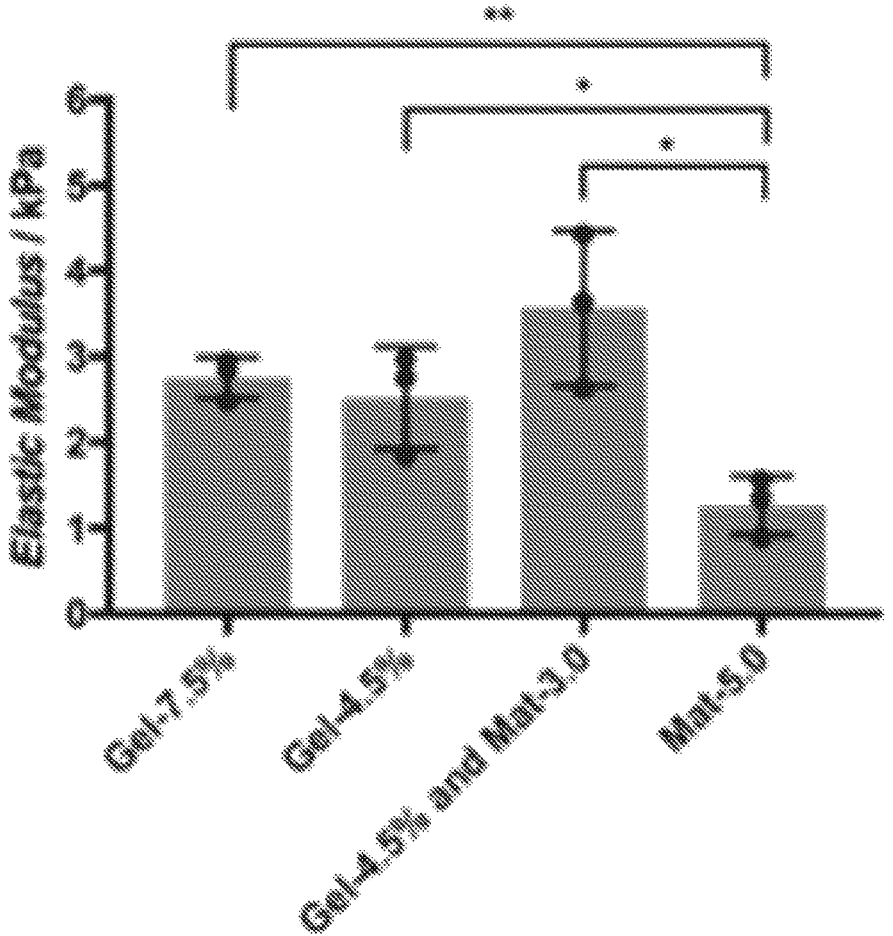

FIG. 21B shows atomic force microscopy measurements, wherein hydrogel stiffness was measured by AFM. Nanoindentations were performed using a pyrex-nitride probe with a pyramid tip connected to a MFP-3D Bio Atomic Force Microscope mounted on a Ti—U fluorescent inverted microscope. After calibration using a glass slide, samples were loaded on the AFM, submersed in phosphate buffered saline (PBS), and indented at a velocity of 2 μm/s with a trigger force of 2 nN.

DETAILED DESCRIPTION

Definitions

Before the present methods are described, it is to be understood that the invention is not limited to the particular methodologies and protocols and apparatuses described, as these may vary. It is also to be understood that the terminology used herein is intended to describe particular embodiments of the present invention, and is in no way intended to limit the scope of the present invention as set forth in the appended claims.

All numerical designations, e.g., pH, temperature, time, concentration, and molecular weight, including ranges, are approximations which are varied (+) or (−) by increments of 0.1 or 1 where appropriate. It is to be understood, although not always explicitly stated that all numerical designations are preceded by the term "about". The term "about" also includes the exact value "X" in addition to minor increments of "X" such as "X+0.1 or 1" or "X−0.1 or 1," where appropriate. It also is to be understood, although not always explicitly stated, that the reagents described herein are merely exemplary and that equivalents of such are known in the art.

Unless defined otherwise, all technical and scientific terms used herein have the same meanings as commonly understood by one of ordinary skill in the art to which this disclosure belongs. Although any methods and materials similar or equivalent to those described herein can be used in the practice or testing of the present invention, the preferred methods, devices, and materials are now described. All technical and patent publications cited herein are incorporated herein by reference in their entirety. Nothing herein is to be construed as an admission that the invention is not entitled to antedate such disclosure by virtue of prior invention.

Throughout and within this application technical and patent literature are referenced by a citation. For certain references, the identifying citation is found at the end of this application immediately preceding the claims. All publications are incorporated by reference into the present disclosure to more fully describe the state of the art to which this disclosure pertains.

The practice of the present disclosure will employ, unless otherwise indicated, conventional techniques of tissue culture, immunology, molecular biology, microbiology, cell biology and recombinant DNA, which are within the skill of the art. See, e.g., Sambrook and Russell eds. (2001) Molecular Cloning: A Laboratory Manual, $3^{rd}$ edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, $5^{th}$ edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; Immobilized Cells and Enzymes (IRL Press (1986)); Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); Herzenberg et al. eds (1996) Weir's Handbook of Experimental Immunology; Manipulating the Mouse Embryo: A Laboratory Manual, $3^{rd}$ edition (Cold Spring Harbor Laboratory Press (2002)); Sohail (ed.)(2004) Gene Silencing by RNA Interference: Technology and Application (CRC Press).

As used in the specification and claims, the singular form "a", "an" and "the" include plural references unless the context clearly dictates otherwise. For example, the term "a cell" includes a plurality of cells, including mixtures thereof.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions of this invention or process steps to produce a composition or achieve an intended result. Embodiments defined by each of these transition terms are within the scope of this invention.

The term "isolated" as used herein with respect to nucleic acids, such as DNA or RNA, refers to molecules separated from other DNAs or RNAs, respectively that are present in the natural source of the macromolecule. The term "isolated nucleic acid" is meant to include nucleic acid fragments which are not naturally occurring as fragments and would not be found in the natural state. The term "isolated" is also used herein to refer to polypeptides, proteins and/or host cells that are isolated from other cellular proteins and is meant to encompass both purified and recombinant polypeptides. In other embodiments, the term "isolated" means separated from constituents, cellular and otherwise, in which the cell, tissue, polynucleotide, peptide, polypeptide, protein, antibody or fragment(s) thereof, which are normally associated in nature. For example, an isolated cell is a cell that is separated form tissue or cells of dissimilar phenotype or genotype. As is apparent to those of skill in the art, a non-naturally occurring polynucleotide, peptide, polypeptide, protein, antibody or fragment(s) thereof, does not require "isolation" to distinguish it from its naturally occurring counterpart.

The term "propagate" or "expand" means to grow a cell or population of cells. The term "growing" also refers to the proliferation of cells in the presence of supporting media, nutrients, growth factors, support cells, or any chemical or biological compound necessary for obtaining the desired number of cells or cell type.

The term "culturing" refers to the in vitro propagation of cells or organisms on or in media of various kinds. It is understood that the descendants of a cell grown in culture may not be completely identical (i.e., morphologically, genetically, or phenotypically) to the parent cell.

As used herein, "stem cell" defines a cell with the ability to divide for indefinite periods in culture and give rise to specialized cells. At this time and for convenience, stem cells are categorized as somatic (adult) or embryonic. A somatic stem cell is an undifferentiated cell found in a differentiated tissue that can renew itself (clonal) and (with certain limitations) differentiate to yield all the specialized cell types of the tissue from which it originated, e.g., adipose-derived stem cell, mesenchymal stem cell, or neuronal stem cell. An embryonic stem cell is a primitive (undifferentiated) cell from the embryo that has the potential to become a wide variety of specialized cell types. An embryonic stem cell is one that has been cultured under in vitro conditions that allow proliferation without differentiation for months to years. A clone is a line of cells that is genetically identical to the originating cell; in this case, a stem cell.

A "composition" is intended to mean a combination of active polypeptide, polynucleotide or antibody and another compound or composition, inert (e.g. a detectable label) or active (e.g. a gene delivery vehicle).

A "pharmaceutical composition" is intended to include the combination of an active polypeptide, polynucleotide or antibody with a carrier, inert or active such as a solid support, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin (1975) Remington's Pharm. Sci., 15th Ed. (Mack Publ. Co., Easton).

A "subject," "individual" or "patient" is used interchangeably herein, and refers to a vertebrate, preferably a mammal, more preferably a human. Mammals include, but are not limited to, murines, rats, rabbit, simians, bovines, ovine, porcine, canines, feline, farm animals, sport animals, pets, equine, and primate, particularly human.

"Host cell" refers not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

"Treating" or "treatment" of a disease includes: (1) preventing the disease, i.e., causing the clinical symptoms of the disease not to develop in a patient that may be predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

The term "suffering" as it related to the term "treatment" refers to a patient or individual who has been diagnosed with or is predisposed to infection or a disease incident to infection. A patient may also be referred to being "at risk of suffering" from a disease because of active or latent infection. This patient has not yet developed characteristic disease pathology.

An "effective amount" is an amount sufficient to effect beneficial or desired results. An effective amount can be administered in one or more administrations, applications or dosages. Such delivery is dependent on a number of variables including the time period for which the individual dosage unit is to be used, the bioavailability of the therapeutic agent, the route of administration, etc. It is understood, however, that specific dose levels of the therapeutic agents of the present invention for any particular subject depends upon a variety of factors including the activity of the specific compound employed, the age, body weight, general health, sex, and diet of the subject, the time of administration, the rate of excretion, the drug combination, and the severity of the particular disorder being treated and form of administration. Treatment dosages generally may be titrated to optimize safety and efficacy. Typically, dosage-effect relationships from in vitro and/or in vivo tests initially can provide useful guidance on the proper doses for patient administration. In general, one will desire to administer an amount of the compound that is effective to achieve a serum level commensurate with the concentrations found to be effective in vitro. Determination of these parameters is well within the skill of the art. These considerations, as well as effective formulations and administration procedures are well known in the art and are described in standard textbooks.

The term "administration" shall include without limitation, administration by oral, parenteral (e.g., intramuscular, intraperitoneal, intravenous, ICV, intracisternal injection or infusion, subcutaneous injection, or implant), by inhalation spray nasal, vaginal, rectal, sublingual, urethral (e.g., urethral suppository) or topical routes of administration (e.g., gel, ointment, cream, aerosol, etc.) and can be formulated, alone or together, in suitable dosage unit formulations containing conventional non-toxic pharmaceutically acceptable carriers, adjuvants, excipients, and vehicles appropriate for each route of administration. The invention is not limited by the route of administration, the formulation or dosing schedule.

As used herein, "encapsulate" means to enclose, include, surround, envelop, cover or contain a material or cell of interest.

As used herein, "evacuable" means removable from any volume, matrix, structure, composite, or, housing using any solvent, aqueous solvent, media, or other evacuant.

As used herein, "filament" means any fabricated material or composite capable of being encapsulated, including, but not limited to, synthetic polymers such as poly-vinyl alcohol.

As used herein, "gelate" means to form a gel or to induce polymerization of a biological or synthetic substance.

As used herein, "perfuse" means to permeate or suffuse any pathway, including but not limited to any vasculature or synthetic lumens, typically with a fluid.

An "Ultimaker" is 3D printer sold and/or manufactured by Dynamism (see dynamism.com/3d-printers/ultimaker-s5.shtml?gclid=EAIaIQobChMIxZzJ-vmR4gIVM_7jBx0JJg8UEAAYASAAEgLVf_D_BwE). Equivalents include any three-dimensional printers that can be used for the generation of tissues.

Non-limiting examples of genome engineering or genetic engineering or transcriptome engineering technologies include CRISPR, ZFN and TALEN nucleases, and RNAi. As used herein, the term "CRISPR" refers to a technique of sequence specific genetic manipulation relying on the clustered regularly interspaced short palindromic repeats pathway. CRISPR can be used to perform gene editing and/or gene regulation, as well as to simply target proteins to a specific genomic location. "Gene editing" refers to a type of genetic engineering in which the nucleotide sequence of a target polynucleotide is changed through introduction of deletions, insertions, single stranded or double stranded breaks, or base substitutions to the polynucleotide sequence. In some aspects, CRISPR-mediated gene editing utilizes the pathways of non-homologous end-joining (NHEJ) or homologous recombination to perform the edits. Gene regulation refers to increasing or decreasing the production of specific gene products such as protein or RNA.

The term "gRNA" or "guide RNA" as used herein refers to guide RNA sequences used to target specific polynucleotide sequences for gene editing employing the CRISPR technique. Techniques of designing gRNAs and donor therapeutic polynucleotides for target specificity are well known in the art. For example, Doench, J., et al. Nature biotechnology 2014; 32(12):1262-7, Mohr, S. et al. (2016) FEBS Journal 283: 3232-38, and Graham, D., et al. Genome Biol. 2015; 16: 260. gRNA comprises or alternatively consists essentially of, or yet further consists of a fusion polynucleotide comprising CRISPR RNA (crRNA) and trans-activating CRIPSPR RNA (tracrRNA); or a polynucleotide comprising CRISPR RNA (crRNA) and trans-activating CRIPSPR RNA (tracrRNA). In some aspects, a gRNA is synthetic (Kelley, M. et al. (2016) J of Biotechnology 233 (2016) 74-83).

The term "Cas9" refers to a CRISPR associated endonuclease referred to by this name. Non-limiting exemplary Cas9s include *Staphylococcus aureus* Cas9, nuclease dead Cas9, and orthologs and biological equivalents each thereof. Orthologs include but are not limited to *Streptococcus pyogenes* Cas9 ("spCas9"), Cas 9 from *Streptococcus* thermophiles, *Legionella* pneumophilia, *Neisseria* lactamica, *Neisseria meningitides, Francisella novicida*; and Cpf1 (which performs cutting functions analogous to Cas9) from various bacterial species including Acidaminococcus spp. and *Francisella novicida* U112.

As used herein, "TALEN" (transcription activator-like effector nucleases) refers to engineered nucleases that comprise a non-specific DNA-cleaving nuclease fused to a TALE DNA-binding domain, which can target DNA sequences and be used for genome editing. Boch (2011) Nature Biotech. 29: 135-6; and Boch et al. (2009) Science 326: 1509-12; Moscou et al. (2009) Science 326: 3501.

TALEs are proteins secreted by *Xanthomonas* bacteria. The DNA binding domain contains a repeated, highly conserved 33-34 amino acid sequence, with the exception of the 12th and 13th amino acids. These two positions are highly variable, showing a strong correlation with specific nucleotide recognition. They can thus be engineered to bind to a desired DNA sequence. To produce a TALEN, a TALE protein is fused to a nuclease (N), which is a wild-type or mutated FokI endonuclease. Several mutations to FokI have been made for its use in TALENs; these, for example, improve cleavage specificity or activity. Cermak et al. (2011) Nucl. Acids Res. 39: e82; Miller et al. (2011) Nature Biotech. 29: 143-8; Hockemeyer et al. (2011) Nature Biotech. 29: 731-734; Wood et al. (2011) Science 333: 307; Doyon et al. (2010) Nature Methods 8: 74-79; Szczepek et al. (2007) Nature Biotech. 25: 786-793; and Guo et al. (2010) J. Mol. Bio. 200: 96. The FokI domain functions as a dimer, requiring two constructs with unique DNA binding domains for sites in the target genome with proper orientation and spacing. Both the number of amino acid residues between the TALE DNA binding domain and the FokI cleavage domain and the number of bases between the two individual TALEN binding sites appear to be important parameters for achieving high levels of activity. Miller et al. (2011) Nature Biotech. 29: 143-8. TALENs specific to sequences in immune cells can be constructed using any method known in the art, including various schemes using modular components. Zhang et al. (2011) Nature Biotech. 29: 149-53; Geibler et al. (2011) PLoS ONE 6: e19509.

As used herein, "ZFN" (Zinc Finger Nuclease) refers to engineered nucleases that comprise a non-specific DNA-cleaving nuclease fused to a zinc finger DNA binding domain, which can target DNA sequences and be used for genome editing. Like a TALEN, a ZFN comprises a FokI nuclease domain (or derivative thereof) fused to a DNA-binding domain. In the case of a ZFN, the DNA-binding domain comprises one or more zinc fingers. Carroll et al. (2011) Genetics Society of America 188: 773-782; and Kim et al. (1996) Proc. Natl. Acad. Sci. USA 93: 1156-1160. A zinc finger is a small protein structural motif stabilized by one or more zinc ions. A zinc finger can comprise, for example, Cys2His2, and can recognize an approximately 3-bp sequence. Various zinc fingers of known specificity can be combined to produce multi-finger polypeptides which recognize about 6, 9, 12, 15 or 18-bp sequences. Various selection and modular assembly techniques are available to generate zinc fingers (and combinations thereof) recognizing specific sequences, including phage display, yeast one-hybrid systems, bacterial one-hybrid and two-hybrid systems, and mammalian cells. Like a TALEN, a ZFN must dimerize to cleave DNA. Thus, a pair of ZFNs are required to target non-palindromic DNA sites. The two individual ZFNs must bind opposite strands of the DNA with their nucleases properly spaced apart. Bitinaite et al. (1998) Proc. Natl. Acad. Sci. USA 95: 10570-5. ZFNs specific to sequences in immune cells can be constructed using any method known in the art. See, e.g., Provasi (2011) Nature Med. 18: 807-815; Torikai (2013) Blood 122: 1341-1349; Cathomen et al. (2008) Mol. Ther. 16: 1200-7; Guo et al. (2010) J. Mol. Bioi. 400: 96; U.S. Patent Publication 201110158957; and U.S. Patent Publication 2012/0060230.

As used herein, "RNAi" (RNA interference) refers to the method of reducing or eliminating gene expression in a cell by targeting specific mRNA sequences for degradation via introduction of short pieces of double stranded RNA (dsRNA) and small interfering RNA (such as siRNA, shRNA or miRNA etc.) (Agrawal, N. et al.; Microbiol Mol Biol Rev. 2003; 67:657-685, Arenz, C. et al.; Naturwissenschaften. 2003; 90:345-359, Hannon GJ.; Nature. 2002; 418:244-251).

"Immune cells" includes, e.g., white blood cells (leukocytes) which are derived from hematopoietic stem cells (HSC) produced in the bone marrow, lymphocytes (T cells, B cells, natural killer (NK) cells) and myeloid-derived cells (neutrophil, eosinophil, basophil, monocyte, macrophage, dendritic cells). "T cell" includes all types of immune cells expressing CD3 including T-helper cells (CD4+ cells), cytotoxic T-cells (CD8+ cells), natural killer T-cells, T-regulatory cells (Treg) and gamma-delta T cells. A "cytotoxic cell" includes CD8+ T cells, natural-killer (NK) cells, and neutrophils, which cells are capable of mediating cytotoxicity responses. Cytokines are small secreted proteins released by immune cells that have a specific effect on the interactions and communications between said immune cells. Cytokines can be pro-inflammatory or anti-inflammatory. Non-limiting example of a cytokine is Granulocyte-macrophage colony-stimulating factor (GM-CSF), which stimulates stem cells to produce granulocytes (neutrophils, eosinophils, and basophils) and monocytes.

As used herein "endothelial cells" refer to cells that form the endothelium lining in blood vessels.

As used herein a "hydrogel" refers to macromolecular materials (large enough to be seen visibly) consisting of a network of polymers, with the majority of its composition being water. A Matrigel hydrogel may consist of 10 mg/mL (1%) Matrigel, with the rest of the body of the material being water. A Matrigel/fibrin hydrogel may consist of 5 mg/mL (0.5%) Matrigel and 10 mg/mL (1%) Fibrin, with the rest of the body of the material being water. In this case, the fibrin is typically polymerized into chains by the enzyme thrombin. A Matrigel/gelatin/fibrin hydrogel may consist of 5 mg/mL (0.5%) Matrigel, 10 mg/mL gelatin (1%) gelatin, and 10 mg/mL (1%) Fibrin, with the rest of the body of the material being water. In this case, the gelatin is typically crosslinked by the enzyme transglutaminase, and the fibrin is typically polymerized into chains by the enzyme thrombin. A collagen hydrogel may consist of 5 mg/mL (0.5%) collagen, with the rest of the body of the material being water. In this case, the collagen is typically crosslinked by the enzyme transglutaminase. At least FIGS. 2A, 2B, 9A, 9B, and 18C provide images wherein one part of the image is a visible hydrogel.

As used herein an "organoid model" refers to a 3D cell culture system that accurately models and incorporates the biological features of the represented organ.

As used herein a "somatic cell" refers to any cell within the body that is not a reproductive cell, or a pluripotent stem cell. Non-limiting examples of somatic cells include: mesenchymal stem cells, hepatocytes, venous endothelial cells, aortic endothelial cells, cardiomyocytes, gut epithelial cells, goblet cells, fibroblasts, and neurons.

Figure 2B:
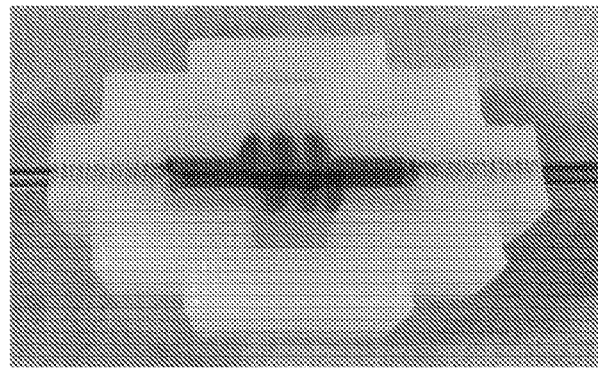
Figure 2C:
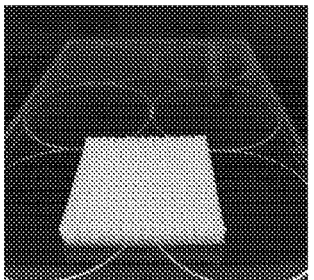
Figure 2D:
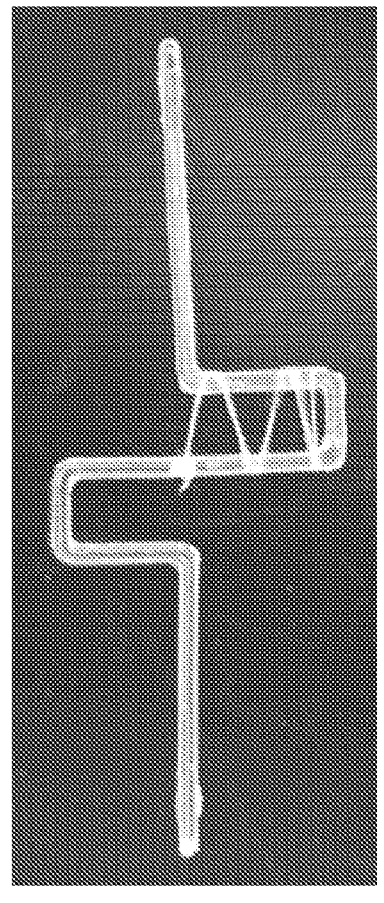

Non-limiting examples of "water-soluble poly-vinyl alcohol structures" can be seen directly in FIG. 2A, which provides four water-soluble poly(vinyl alcohol) structures, before and after being solvated in water. FIGS. 2C and 2D provide structures before solvation. FIG. 18B provides a series of images displaying the solvation of a poly(vinyl alcohol) structure over 60 minutes.

As used herein "free-standing" refers to structures that, if placed in any position, will retain their shape without the need for support from any external structures. At least FIGS. 2A, 2C, and 3, but not limited to these Figures, provide images of free-standing scaffolds used for the creation of the tissue constructs.

As used herein a "vascular pattern" refers to any hollow lumen that can potentially be seeded with endothelial cells. Physically speaking, they are all simply hollow channels. Non-limiting examples of "vascular patterns" or "perfusable lumen patterns" without cells are shown in FIG. 2A, 2B. Non-limiting examples of "vascular patterns" or "perfusable lumen patterns" with cells are shown in FIG. 11A, 11D, 12, 13.

As used herein "solvation" refers to the act by which a solute (typically a solid) has its molecules surrounded and complexed by a solvent (typically a liquid). In partial solvation, only a portion of a bulk solute material has its molecules surrounded and complexed by the solvent. In complete solvation, the entirety of the bulk solute material has its molecules surrounded and complexed by the solvent. Non-limiting examples of partial solvation and complete solvation can both be seen in FIG. 18B, where timepoints 10 minutes and 30 minutes indicate partial solvation, and timepoint 60 minutes indicates complete solvation.

EDTA commonly chelates metal ions. Materials that are reliant on crosslinking by divalent metal cations can be dissolved in EDTA solution. Two common biopolymers that can be dissolved in this manner are alginate (calcium alginate) and pectinate (calcium pectinate).

As used herein an "extrusion printer" refers to extrusion printers that do not use fused-filament printing methods. Non-limiting examples of extrusion printers include Bio-Bot1 (BioBots), Inkredible (CELLINK), and Alpha & Omega (3Dynamic Systems).

As used herein "knitting threads" refer to physically arranging threads into a desired shape or structure. These shapes may include lines, sinusoids, and grids, among others. This action does not require the actual use of knitting needles, but can be accomplished with them if necessary. A non-limiting example of a knitting thread is shown in FIG. 2D.

As used herein, "pharmacological agents" refer to any biologically active substance that may or may not be commercially available. Non-limiting examples of this include: pharmaceuticals, such as Paclitaxel and Veliparib; pharmaceuticals conjugated with nanoparticles, such as Abraxene; small biomolecules, such as Sphingosine-1-Phosphate or Phorbol 12-myristate 13-acetate; growth Factors, such as fibroblast growth factor, or human epidermal growth factor; other molecules, such as heparin, or cholera toxin.

As used herein, "highly dense vasculature" refers to a series of perfusable lumens created by endothelial cells, with both size and separation distance on the order of less than 100 micrometers. A non-limiting example of highly dense vasculature is shown in FIG. 14.

As used herein, non-limiting examples of "pro-angiogenic biomolecules" may include sphingosine-1-phosphate, phorbol 12-myristate 13-acetate, vascular endothelial growth factor, fibroblast growth factor, angiopoietin 1, and angiopoietin 2, among others.

As used herein, "organoid models" may be multicellular three-dimensional constructs with some degree of cell-level organization that are generated in vitro, but mimic the properties of an organ in vivo. A non-limiting example of a tumor organoid is shown in FIG. 15. An example of a gut organoid is shown in FIG. 17B.

As used herein, non-limiting examples of "specific geometries" may include sinusoids, spirals, branched networks, and grids.

As used herein, "transcriptome engineering technologies" may refer to any techniques used to directly modify the RNA of a cell. Common non-limiting variants of this include the use of cytidine deaminases (CDAR) and adenosine deaminases (ADAR).

Modes for Carrying Out the Disclosure

The present disclosure provides a series of methodologies for generating perfusable tissue models in vitro using free-standing evacuable structures and blends of extracellular matrix substitutes optimized for both maintaining structural stability and providing a suitable environment for cell growth. The presence of a perfusable network allows for scaling of the model to sizes proportional to the magnitude of the network dimensions, and further allows for maintenance of excised tissue fragments for sustained culture ex vivo. Moreover, the ability to produce a large variety of patterns for the free-standing evacuable structures allows for construction of tissue models with highly specific shapes and arrangements of cell growth.

Fundamentally, all methods described rely on separately generating a free-standing evacuable structure in a specific desired geometry, and preparing a solution comprising a mixture of viable cells suspended in a liquid-phase extracellular matrix substitute, or blend of extracellular matrix substitutes. The evacuable structure is subsequently encapsulated within the cell-suspending mixture, which is allowed to fully gelate over a defined period of time. Following completion of gelation, the free-standing structure is dissolved and evacuated, yielding a hollow lumenal network within the cell-encapsulating gel construct. The network is subsequently perfused with growth media specific to the cell types within the construct, and can be seeded with different cell types to mimic in vivo tissue structures. Examples may include human or animal endothelial cells to mimic vasculature, or human or animal intestinal epithelial cells to mimic the gut. This methodology is fully described in FIG. 1A, with variations described in FIG. 1B and FIG. 1C.

FIGS. 1A to 1C: (FIG. 1A) depict schematics for describing the main steps in the construction of a perfusable tissue construct. A free-standing scaffold is generated independently of the construct and is placed within an enclosed container. An extracellular matrix substitute solution is subsequently deposited over the construct, and is allowed to transition to gel phase. The construct is then sealed, and the scaffold is dissolved and evacuated. The resulting lumen is perfused with cell growth media, and can be seeded with a desired cell type by the user. (FIG. 1B) Schematic describing a modification to the construction of a perfusable tissue construct to produce vascular lumens of greater density. All steps are identical to those described in FIG. 1A, but the free-standing scaffold is modified via wrapping of water-soluble poly-vinyl alcohol-based threads that are able to be evacuated along with the main scaffold. (FIG. 1C) Schematic describing the main steps in the construction of a perfusable tissue construct capable of interstitial flow. Methodology is identical to that described in FIG. 1A, but encapsulation, evacuation, and perfusion take place in a double-chambered container, with the matrix only being added to the inner container.

In one aspect, the disclosure provides a methodology that allows for the production of three-dimensional biocompatible matrices penetrated by highly specific lumenal patterns and geometries. This can be accomplished with or without cells or primary tissue fragments encapsulated within the matrix, and with or without cells lining the interior of the lumens. The presence of the biocompatible matrix allows for growth and sustenance of encapsulated of cells or excised tissue fragments in an environment that mimics native extracellular matrix conditions, while the lumenal patterns allow for perfusion and sustenance of the system with growth media or biomolecules in a manner that scales with the specific patterns being used.

Specifically, the disclosure allows for construction of a solid but evacuable free-standing structure that can take the form of various 2D or 3D printed geometries including linear channels, sinusoids, grids, and spirals among others. This free-standing structure can subsequently be surrounded by a cell encapsulating solution of biological matrix or matrix-substitute such as Matrigel, gelatin, collagen, fibrin, or a blend of any of the aforementioned. Following enclosure in an aqueous matrix solution, the matrix solution is permitted to gelate to create a cellularized matrix. Subsequently, the free-standing structure can be evacuated to form a hollow channel that can be used to perfuse the matrix with media. This channel can also be seeded with endothelial cells to imitate biological vasculature. Perfusion of the matrix through the evacuated vascular channels allows for both the design and sustenance of and growth of the cells within thick, tissue constructs for period exceeding 30 days. Furthermore, perfusion also allows for the sustenance of human primary tissue fragments embedded in the matrix for identical durations, and promotes angiogenic sprouting of embedded endothelial cells.

Overall, the result is a system that is able to do one or more, or all of the following:

Sustains cells of a specific type over time.
Sustains cells of multiple types over time.
Sustains tissue fragments of a specific type over time.
Sustains tissue fragments of multiple types over time.
Allows for generation of encapsulated lumens of specific geometries.
Allows for perfusion of lumen-encapsulating matrices of specific geometries.
Generates lumens that may be seeded with endothelial or epithelial cells in specific geometries.
Allows for exposure of endothelial or epithelial cells to specific flow rates.
Allows for 3D culture of cells or excised tissue in specific geometries.
Provides a 3D microenvironment that mimics in vivo extracellular matrix.
Allows for 3D coculture of multiple cell types or excised tissue in an environment that mimics extracellular matrix.
Allows for selective treatment of encapsulated cells or excised tissue with specific biomolecules.
Allows for the generation of organoid-like structures from excised tissue or primary stem cells in specific geometries.
Allows for rapid and replicable reproduction of a system capable of all of the above.

Method of Generating Free-Standing Evacuable Vascular Scaffolds

In one aspect, a method of generating cellularized ex vivo tissue constructs is provided herein, the method comprising: (i) suspending a plurality of viable cells and/or a plurality of tissue fragments in a liquid-phase hydrogel to prepare a composite and/or solution; (ii) encapsulating a free-standing evacuable filament structure within the composite and/or solution; (iii) gelating the composite and/or solution to mimic a cellular matrix; and (iv) dissolving and evacuating the free-standing filament structure to create at least one lumen in the cellular matrix. The free-standing evacuable filament structure can be poly-vinyl alcohol and can be three-dimensionally printed, stable in air, and dissolvable in an aqueous solvent. Alginate-pluronic structures can be single-way channels comprising sinusoidal and linear channels. In some embodiments, the filament structure can be single-way channels in a three-dimensional structure selected from helical, sinusoidal, and linear channel. In some embodiments, the filament structure can be multi-way channels in a three-dimensional structure selected from cubical, grid, or a spherical channel.

In some embodiments, the filament structure can be of any general singular multi-channel configuration capable of being printed by a 3D printer. In some embodiments, the filament structure comprises two or more water soluble poly-vinyl alcohol structures within the same construct. In some embodiments, the freestanding evacuable filament structure can be encapsulated by use of a micropipette to form a vascular pattern interpenetrating the one or more tissue patterns. The method can include removing the poly-vinyl alcohol by partial solvation within the encapsulating matrix, followed by attaching the tissue construct to a peristaltic pump and perfusing for about 10-20 minutes. The polyvinyl alcohol can be removed by partial solvation within the encapsulating matrix, followed by manual perfusion using a pipette. The method can also include removing the polyvinyl alcohol by complete solvation within the encapsulating matrix, and gradual removal via bathing and incubation in aqueous media. Partial solvation can be done using cell growth media as the solvent to remove the polyvinyl alcohol.

The three-dimensionally printed free-standing structure can include alginate and pluronic blend, and wherein a composite material is dissolvable in an EDTA solvent. The methods further may include cross-linking the composite material via submersion in a calcium chloride solution at a concentration between about 5 to about 250 mM immediately following extrusion. In some embodiments, the method further includes depositing a base matrix layer on a substrate before inserting the alginate-pluronic vasculature structure, wherein a top layer of matrix is poured over the vasculature structure to ensure that the evacuable filament is embedded between two matrix layers. The alginate-pluronic structures can also be single-way channels comprising sinusoidal and linear channels. In some embodiments, the alginate-pluronic structures can be multi-way channels comprising cubical and grid-shaped channels.

The alginate-pluronic structures can also be any general singular multi-channel configuration capable of being generated by an extrusion printer. In some embodiments, the alginate-pluronic structure is removed by incubating in about 2 degrees Celsius to about 8 degrees Celsius to liquefy a pluronics component, followed by evacuation with cold media containing EDTA by micropipettes. Knitting threads may be constructed by the poly-vinyl alcohol into an evacuable, free-standing filament structure, where the material is stable in air and dissolvable in an aqueous solvent. The polyvinyl alcohol can also be removed by partial solvation within the encapsulating matrix, followed by attaching the tissue construct to a peristaltic pump and perfusing for about 10 to about 20 minutes. The polyvinyl alcohol can also be removed by partial solvation within the encapsulating matrix, followed by manual perfusion using a pipette. In some embodiments of the methods, the polyvinyl alcohol can be removed by complete solvation within the encapsulating matrix, and gradual removal via bathing and incubation in aqueous media.

Any form of cell growth media can be used as the solvent to remove the polyvinyl alcohol. Any of the previously disclosed methods may also be used in combination. The composite and/or hydrogel designed to mimic the extracellular matrix can be at least one of matrigel, fibrin, gelatin, bovine collagen, porcine collagen, rat-tail collagen, gelatin methacrylate, alginate, decellularized extracellular matrix, or polyethylene glycol, and also can be any combination thereof. In certain embodiments of the method, the combination of materials comprises about 1.5 mg/mL gelatin, about 4.0 mg/mL matrigel, and about 10 mg/mL fibrin.

One or more viable human or non-human cell types can also be encapsulated within the construct. Combinations of human and non-human cell types can also be encapsulated within the construct. The interior lumen or lumens of the construct can also be perfused with cell growth media. In some embodiments, two or more distinct interior lumens of the construct can be perfused with distinct types of cell growth media. One or more viable human or non-human endothelial or epithelial cell types can be used to coat the interior lumen of the construct following evacuation of the free-standing structure. One or more different viable human or non-human endothelial or epithelial cell types are used in distinct lumens of the construct following evacuation of the free-standing structure.

The cell growth medium or media used to perfuse the interior of the lumen or lumens of the construct can contain biological molecules or nanoparticles, including but not limited to growth factors, steroids, carbohydrates, cytotoxins, and amino acids. Extracellular matrix binding proteins, including but not limited to laminin and fibronectin, may be used to precoat the interior lumen of the construct following evacuation of the free-standing structure, but preceding the addition of endothelial or epithelial cell types. Fragments of excised tissue may also be encapsulated within the body of the matrix construct. The construct can also be generated in replicate and treated with pharmacological agents, or human or non-human derived immune cells.

The disclosed methods may be used to generate at least one of: (i) an in vitro model of a tumor directly via encapsulation and perfused sustenance of primary tumor cells or a carcinoma cell line within the matrix; (ii) an ex vivo model of a tumor via embedding and perfused sustenance of excised tumor fragments within the matrix; (iii) an in vitro model of highly dense vasculature via seeding of human or animal endothelial cells within one or more lumens, encapsulation of human or animal endothelial cells within the matrix, and the addition of pro-angiogenic biomolecules or a gradient of pro-angiogenic biomolecules; (iv) an in vitro model of a gut via seeding and sustenance of primary intestinal epithelial cells or an intestinal epithelial cell line within one or more lumens; (v) any additional organoid models via seeding and sustenance of primary somatic cells, cell lines, or primary stem cells either within the lumen or within the matrix body; (vi) exposing endothelial or epithelial cells to physiological flow rates or specific flow rates, wherein the physiological flow rates or the specific flow rates optionally are 0.01-100 mL/min; (vii) three-dimensionally cocultured multiple cell types or excised tissue in an environment that mimics extracellular matrix; (viii) organoid-like structures from excised tissue or primary stem cells in specific geometries; (ix) a construct comprising MDA-MB-231 cells in a stroma, further comprising post-evacuation seeding of endothelial cells, and long-term perfusion to generate a tumor organoid.

The cells used for the construct can be genetically modified to allow for the conduction of genetic screens using CRISPR or other genome engineering or transcriptome engineering technologies.

Figure 5A:
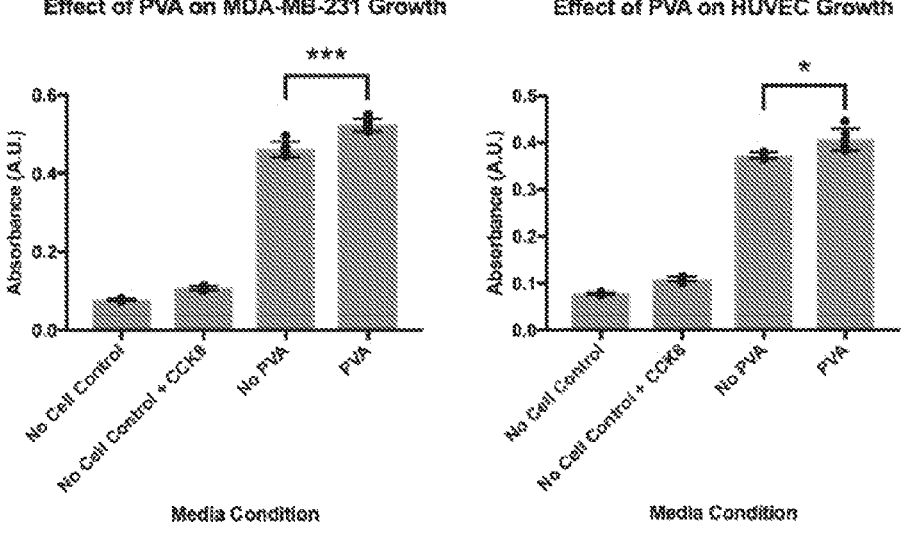
FIGS. 5A-5B.
Figure 5B:
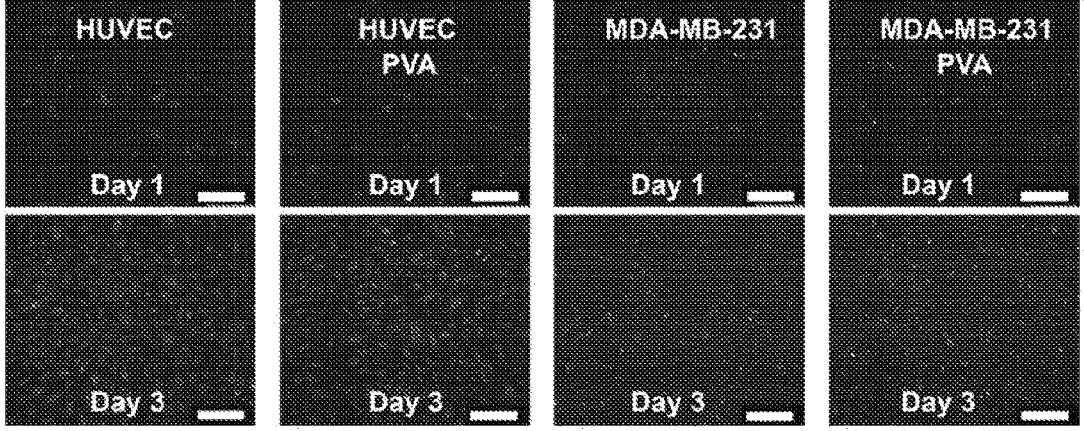

A free-standing evacuable filament structure can be generated using a commercial 3D printer, an example of which is the Ultimaker[3], to extrude poly-vinyl alcohol (PVA) in a pre-programmed pattern. In some embodiments, the free-standing evacuable filament structure can be graphene filaments (e.g., as manufactured by "Black Magic 3D"), "Hydrosupport," or other commercially available water-soluble synthetic polymers. Structures can be patterned in both one and two dimensions, or free-standing patterns in three dimensions. Because of existing hygroscopic properties of the material, the PVA must be stored in a moisture-limited environment, which can be accomplished with the use of desiccating agents. Alterations of printing parameters can produce a wide range of evacuable structures. Several examples of these, spanning across a variety of geometries, are shown in FIG. 2. All structures are able to have overall dimensions and density modified, and can subsequently be dissolved in any aqueous solvent, including but not limited to water, phosphate-buffered saline, and cell culture media. Cytocompatibility of PVA with human cell types has been tested, and the presence of PVA in solution has been demonstrated to have no negative impact on cell growth. This is shown in FIGS. 5A and 5B.

In one embodiment, the scaffold comprises, or alternatively consists essentially of, or yet further consists of a linear rod composed of PVA with variable length and thickness.

In one embodiment, the scaffold comprises, or alternatively consists essentially of, or yet further consists of a sinusoid or square-wave pattern composed of PVA with variable amplitude, period, length, and thickness.

In one embodiment, the free-standing scaffold comprises, or alternatively consists essentially of, or yet further consists of a sum of sinusoids composed of PVA with variable amplitude, period, length, and thickness.

In one embodiment, the free-standing scaffold comprises, or alternatively consists essentially of, or yet further consists of a spiral composed of PVA with variable pitch, width, length, and thickness.

In one embodiment, the free-standing scaffold comprises, or alternatively consists essentially of, or yet further consists of a series of branched channels composed of PVA with varying length, width, and thickness.

In one embodiment, the free-standing scaffold comprises, or alternatively consists essentially of, or yet further consists of a grid composed of PVA with varying density, width, length, and thickness.

Additional embodiments comprise, or alternatively consist essentially of, or yet further consist of free-standing scaffolds generated in additional, more complex geometries than those described thus far. An example of a highly complex free-standing printed PVA structure is shown in FIG. 2C.

Figure 3:
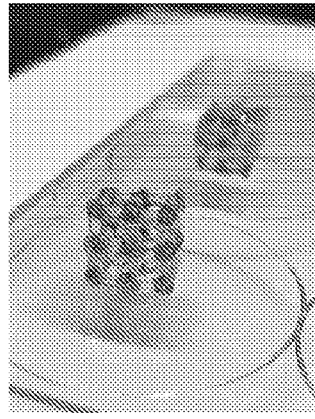
FIG. 3: An example of a free-standing scaffold pattern in the form of a 3D grid, generated via extrusion printing using a blend of about 0.5% alginate and about 40% Pluronics F127, and crosslinked in 20 mM calcium chloride solution.

An evacuable vascular scaffold can be generated using a 3D printer (Aerotek) to extrude a blend of alginate (Variable Molecular Weight, MP Biomedical) and Pluronics F127, followed by brief submersion in a calcium-chloride bath. Concentrations of alginate can range from about 0% to about 2.0%, or alternatively about 0.25% to about 2.0%, or alternatively about 0.5 to about 2.0%, Concentrations of Pluronics can range from about 0% to about 40%, or alternatively about 10% to about 40%, or alternatively about 20% to about 40% for Pluronics F127, all dissolved in water. Structures can be patterns in both one and two dimensions, or free-standing patterns in three dimensions. An example of an evacuable three-dimensional grid structure is shown in FIG. 3. Alterations of printing parameters can produce various two-dimensional structures, as well as free-standing three-dimensional grids. The structures are able to have overall structural dimensions modified, and can subsequently be dissolved in any aqueous, calcium-free solvent containing about 20 mM EDTA at a temperature between about 0° C. to about 8° C., or alternatively about 0° C. to about 6° C., or alternatively between 0° C. to about 4° C.

In one embodiment, the scaffold comprises, or alternatively consists essentially of, or yet further consists of a linear rod composed of an alginate/Pluronics F127 blend with variable length and thickness.

In one embodiment, the scaffold comprises, or alternatively consists essentially of, or yet further consists of a helical, sinusoid or square-wave pattern composed of an alginate/Pluronics F127 blend with variable amplitude, period, length, and thickness.

In one embodiment, the scaffold comprises, or alternatively consists essentially of, or yet further consists of a zig-zag, a cube, or a sphere composed of an alginate/Pluronics F127 blend with variable amplitude, period, length, and thickness.

In one embodiment, the free-standing scaffold consists of a grid composed of an alginate/Pluronics F127 blend with varying density, width, length, and thickness.

Additional embodiments can comprise, or alternatively consist essentially of, or yet further consist of free-standing scaffolds generated in additional, more complex geometries than those described thus far.

An evacuable vascular scaffold can be generated by weaving and arranging threads composed of PVA into specific desired patterns. An example of a thread of this type is the commercially available Solvron. All structures are able to have overall dimensions and density modified based on the quantity of thread used. Because the threads possess the same physical and chemical properties as PVA, they can subsequently be dissolved in any aqueous solvent, including but not limited to water, phosphate-buffered saline, and cell culture media.

In one embodiment, the scaffold comprises, or alternatively consists essentially of, or yet further consists of a linear rod of PVA thread with variable length and thickness.

In one embodiment the scaffold comprises, or alternatively consists essentially of, or yet further consists of a sinusoid composed of PVA thread with variable amplitude, period, length, and thickness.

In one embodiment, the scaffold comprises, or alternatively consists essentially of, or yet further consists of a woven grid composed of PVA thread with variable density, width, length, and thickness.

Additional embodiments can comprise, or alternatively consist essentially of, or yet further consist of free-standing scaffolds generated in additional, more complex geometries than those described thus far. Alternatively, embodiments can comprise, or alternatively consist essentially of, or yet further consist of wrapping individual or multiple weaved PVA threads around free-standing scaffolds of PVA to generate evacuable structures comprising, or alternatively consisting essentially of, or yet further consisting of, a single main channel, with accompanying smaller, narrower channels. An example of a complex, multi-channel evacuable scaffold generated by wrapping PVA threads around an existing free-standing scaffold of PVA is shown in FIG. 2D, and a schematic showing the outcome when evacuated is shown in FIG. 1B.

Figure 4:
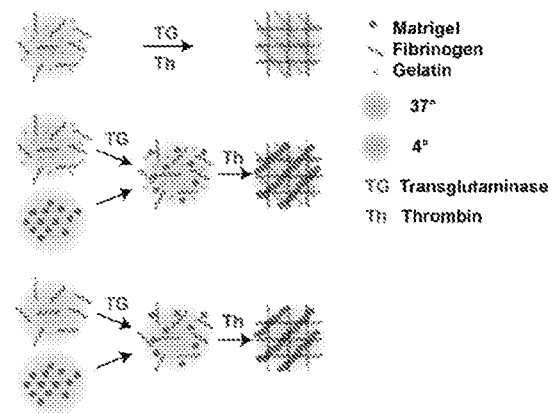
FIG. 4: Method of formulation of various extracellular matrix substitutes. Specifically outlined are methods of generating extracellular matrix substitutes composed of a mixture of gelatin and fibrinogen, Matrigel and fibrinogen, and a blended composite and/or solution of gelatin, Matrigel, and fibrinogen.
Figure 6:
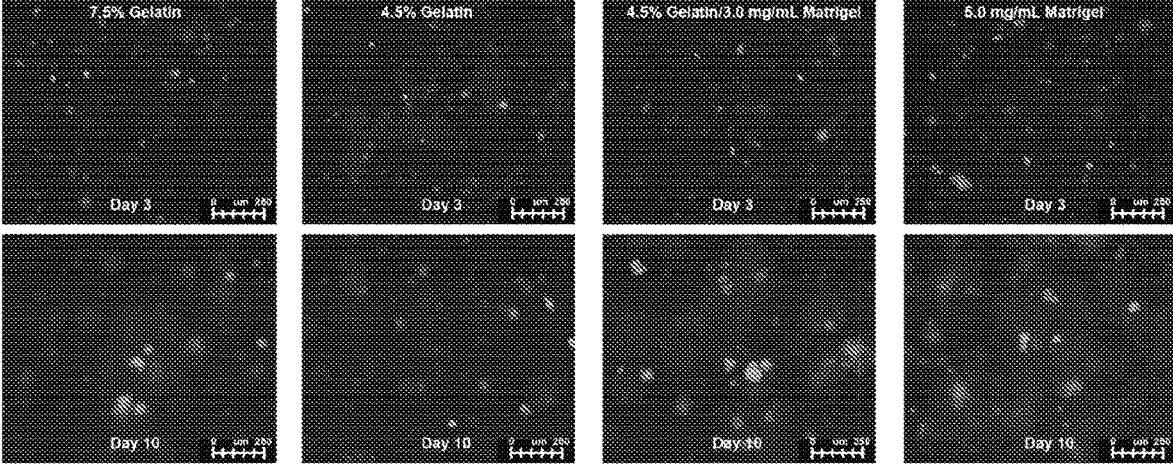
FIG. 6: Qualitative experimental results in which MCF7 breast carcinoma cells were grown in 3D culture over 10 days following encapsulation in matrices of different compositions. All matrices contained about 10 mg/mL fibrin, along with one of the following: about 7.5% gelatin, about 4.5% gelatin, about 4.5% gelatin and about 3 mg/mL Matrigel, about 5 mg/mL Matrigel. Cells were GFP-labeled, and images were obtained using a Widefield Microscope.

Method of Generating an Extracellular Matrix Substitute: Composition and Materials An extracellular matrix substitute can be generated from biocompatible materials with temperature-responsive or enzyme-responsive gelation behavior. Examples of such include, without limitation, gelatin, collagen, fibrin, matrigel, gelatin methacrylate, alginate, hyaluronic acid, and Polyethylene Glycol. Materials in liquid phase are subsequently poured into a mold and allowed to gelate to form a cell-encapsulating matrix. Matrices can comprise, or alternatively consist essentially of, or yet further consist of a single biocompatible material, or blended combinations of multiple materials. All embodiments below can optionally comprise, or alternatively consist essentially of, or yet further consist of the addition of transglutaminase enzyme supplemented with calcium chloride to induce crosslinking of suspended proteins. An outline of the methodology of formulating several variants of such extracellular matrix substitutes is described in FIG. 4. Multiple growth experiments were conducted in which different cell lines were grown in 3D culture in matrices of varying compositions, with net growth and survivability being compared afterwards. The results of these experiments are shown in FIGS. 6-8.

In addition to the essential structural components, matrices can be used to resuspend cells of interest, or a variety of biological chemical compounds. Viable cell types encapsulated within the matrix substitute can include mammalian cells of any type, including those of cell lines, as well as primary germ cells, somatic cells, and stem cells. Examples include, but are not limited to, human embryonic stem cells, human induced pluripotent stem cells, human mesenchymal stem cells, human aortic endothelial cells, human umbilical vein endothelial cells, 293T cells, MDA-MB-231 cells, Caco-2 cells, and MCF-7 cells, Referenced cell lines can be acquired from the American Type Culture Collection (ATCC). Chemical compounds can include drugs, proteins, hormones, and other biological molecules of interest. Examples include, but are not limited to VEGF, SPA-1, PMA, and bFGF. Commercial vendors of the growth factors include, but are not limited to, Lonza for VEGF and bFGF, and Sigma for PMA and SPA-1. Again, viability is maintained following encapsulation, as demonstrated in FIGS. 6-8.

In one embodiment, the extracellular matrix substitute comprises, or alternatively consists essentially of, or yet further consists of a structural blend of Matrigel and fibrinogen with respective protein concentrations between about 0.5-10 mg/mL to about 0.5-20 mg/mL. Thrombin is subsequently added to induce polymerization of fibrinogen into a fibrin network, while matrigel gelates in response to heating to at about 20° C. or above, or, alternatively at about 37° C. to maintain cell viability.

In one embodiment, the extracellular matrix substitute is composed structurally of Matrigel alone, with a respective protein concentration between about 0.5 to about 10 mg/mL. Gelation is induced in response to heating to about 37° C.

In one embodiment, the extracellular matrix substitute is composed structurally of fibrinogen alone, with a respective protein concentration between about 0.5 to about 20 mg/mL. Thrombin is subsequently added to induce polymerization of fibrinogen into a fibrin network.

In one embodiment, the extracellular matrix substitute is composed structurally of a blend of gelatin, Matrigel, and fibrinogen. Gelatin content can range from about 0.5 to about 7.5%, while Matrigel and fibrinogen protein concentrations can range between about 0.5 to about 10 mg/mL and about 0.5 to about 20 mg/mL. Thrombin is subsequently added to induce polymerization of fibrinogen into a fibrin network, while matrigel gelates in response to heating to about 37° C.

In one embodiment, the extracellular matrix substitute is composed structurally of a blend of gelatin, Type I bovine collagen, and fibrinogen. Gelatin content can range from about 0.5 to about 7.5%, while collagen and fibrinogen protein concentrations can range between about 0.5 to about 10 mg/mL and about 0.5 to about 20 mg/mL. Thrombin is subsequently added to induce polymerization of fibrinogen into a fibrin network, while collagen gelates in response to heating to about 37° C.

In one embodiment, the extracellular matrix substitute is composed structurally of a blend of Type I bovine collagen alone, at concentrations between about 0.5 to about 10 mg/mL. Gelation is induced in response to heating to about 37° C.

In one embodiment, the extracellular matrix substitute is composed structurally of a blend of Type I bovine collagen and fibrinogen. Protein concentrations respectively can range between about 0.5-10 mg/mL and 0.5-20 mg/mL. Thrombin is subsequently added to induce polymerization of fibrinogen into a fibrin network, while collagen gelates in response to heating to about 37° C.

In one embodiment, the extracellular matrix substitute is composed structurally of a blend of gelatin and fibrinogen. Gelatin content can range from about 0.5 to about 7.5%, while fibrinogen protein concentrations can range between about 0.5 to about 20 mg/mL. Thrombin is subsequently added to induce polymerization of fibrinogen into a fibrin network.

Alternative embodiments include, but are not limited to, matrix substitutes composed structurally of gelatin methacrylate, bovine collagen of various types, porcine collagen of various types, rat-tail collagen of various types, alginate, polyethylene glycol, decellularized extracellular matrix, lyophilized decellularized extracellular matrix, or any combinations thereof.

Method of Generating a Perfusable Matrix Construct

In order to generate a perfusable matrix construct, extracellular matrix substitutes in any of the embodiments described above are formulated in liquid phase, with or without additional cells and chemical compounds suspended within. The extracellular matrix substitute solutions are poured over solid-phase evacuable scaffolds and are allowed to transition into a gel-phase. The encapsulated evacuable scaffolds are subsequently dissolved and evacuated from the structure. A working schematic of this process is shown in FIG. 1A and FIG. 1C.

One set of embodiments can be generated via a combination of any of the free-standing evacuable scaffolds and any of the extracellular matrix substitute formulations described previously. Examples of perfused constructs of this nature are shown in FIG. 2A.

One set of embodiments can be generated via the use of multiple free-standing evacuable scaffolds and any of the extracellular formulations described previously. An example of a perfused construct generated from multiple free-standing evacuable scaffolds is shown in FIG. 2B.

One set of embodiments may be generated by encapsulating and evacuating scaffolds, as described previously, from within a single enclosed chamber. Embodiments of this nature are specifically described in the schematic of FIG. 1A.

One set of embodiments may be generated by encapsulating and evacuating scaffolds, as described previously, from within a construct containing two or more chambers. In such cases, the container consists of both an inner chamber and outer chamber, with the matrix solution being poured into and gelating within the inner chamber only. The inner chamber is constructed from a ring of hydrophobic pillars. Fluids poured within the inner chamber retain their shape via surface tension. The outer chamber is constructed from solid, gap-free walls. Together, the inner and outer chamber allow for free flow of fluid through the entirety of the porous matrix during perfusion, generating interstitial flow and pressure. Embodiments of this nature are specifically described in the schematic of FIG. 1C.

Prior to the liquid-phase to gel-phase transition, matrix substitutes can be used to encapsulate various types of stromal, somatic, or pathological cell types to be sustained in vitro over an extended period of time. FIG. 15 shows a matrix composed of about 15 mg/mL gelatin, about 4 mg/mL Matrigel, and about 10 mg/mL fibrin polymerized by both transglutaminase and thrombin, and used to encapsulate cells from the MDA-MB-231 cell line. Growth over time resulted in the formation of cell colonies and compact tumor organoid-like structures.

Figure 10B:
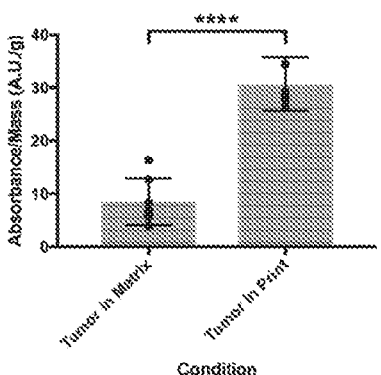
Figure 10C:
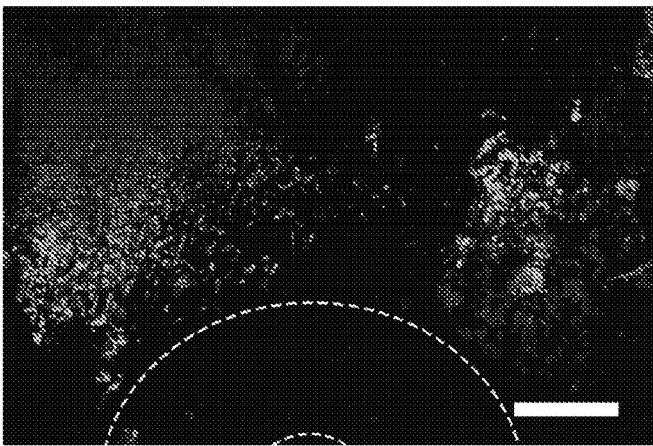
Figure 10D:
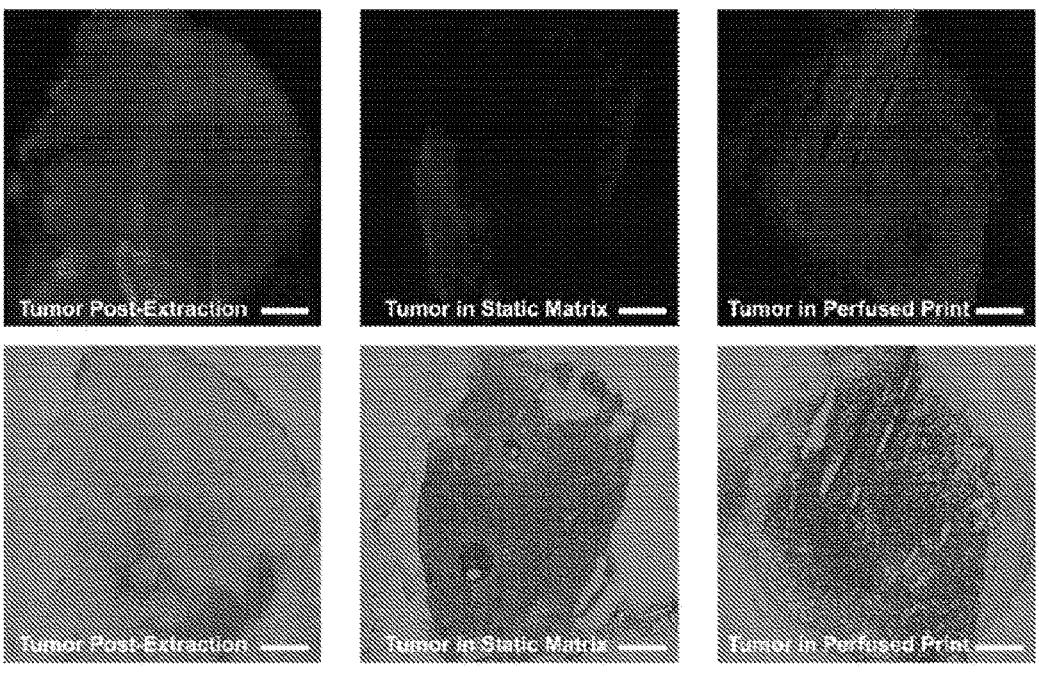

Prior to the liquid-phase to gel-phase transition, matrix substitutes can be embedded with excised tissue fragments to be sustained ex vivo over an extended period of time. FIG. 9A shows a matrix composed of about 15 mg/mL gelatin, about 4 mg/mL Matrigel, and about 10 mg/mL fibrin polymerized by both transglutaminase and thrombin, and embedded with multiple fragments of human breast cancer tumors grown from the MDA-MB-231 cell line. In contrast, FIG. 9B shows a matrix composed of about 5 mg/mL Matrigel and about 10 mg/mL fibrin polymerized by both transglutaminase and thrombin, with no ex vivo tissue fragments added. FIG. 10A shows the quantitative metabolic activity of ex vivo sustenance of multiple fragments of human induced pluripotent stem cell teratomas over a 40-day period in a perfused matrix of matrigel and fibrin. FIG. 10B shows the quantitative metabolic activity of ex vivo sustenance of multiple fragments of tumors (generated from GFP-labeled MDA-MB-231 cells in mice) over a 20-day period in a perfused matrix of gelatin, matrigel and fibrin. FIG. 10C shows qualitative data regarding the morphologies of the MDA-MB-231 tumor fragments within the perfused matrix, corresponding to FIG. 10B. FIG. 10D shows qualitative data regarding survival of MDA-MB-231 tumor fragments within the perfused matrix, in comparison to initial survival, as well as survival in non-perfused matrices. Stated another way, FIG. 10D further shows the qualitative experimental results from the experiment described in FIG. 10B. Following extraction, tumors were embedded in Optimal Cutting Temperature (OCT) compound, cryosectioned, and imaged via Widefield Microscopy at 490 nm as well as under brightfield settings. Magnitude of green fluorescence correlates to proportion of still-living tissue. Scalebars represent 500 µm In embodiments containing a scaffold of 3D-printed PVA patterns or woven PVA threads, an incubation time is provided at about 37° C. following pouring of the liquid phase extracellular matrix substitute in order to allow the water-soluble scaffold to dissolve. Subsequently, the liquefied scaffold is evacuated using aqueous solution. Viable solutions include but are not limited to PBS, water, and cell growth media of any type. The solutions can be delivered via pipetting, or via a peristaltic pump. Alternatively, the entirety of the structure can be submerged in a bath of cell growth media for about 12-48 hours, and the PVA can be allowed to gradually dissolve and diffuse out of the matrix over time.

In embodiments containing a scaffold composed of an alginate/Pluronics F127 blend, an incubation time is provided at about 37° C. to allow the matrix construct to fully gelate. Subsequently, the construct is incubated for about 15-30 minutes at about 4° C. to liquefy the Pluronics F127 component of the blend, and is perfused with a calcium-free solution containing about 5-100 mM EDTA in order to de-crosslink the alginate component of the blend. The solutions can be delivered via pipetting, or via a peristaltic pump.

Figure 11A:
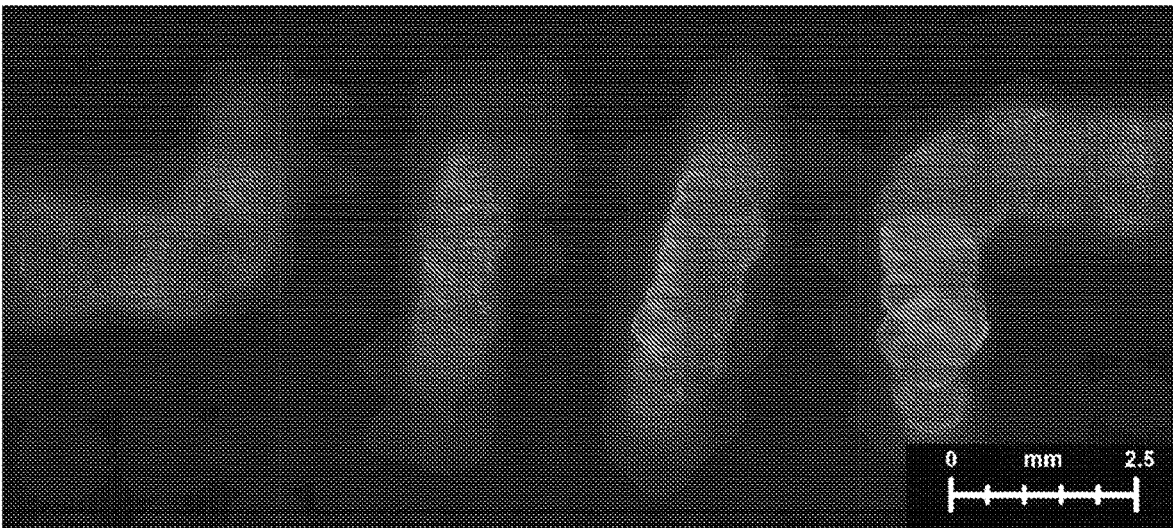
FIGS. 11A-11D.
Figure 11B:
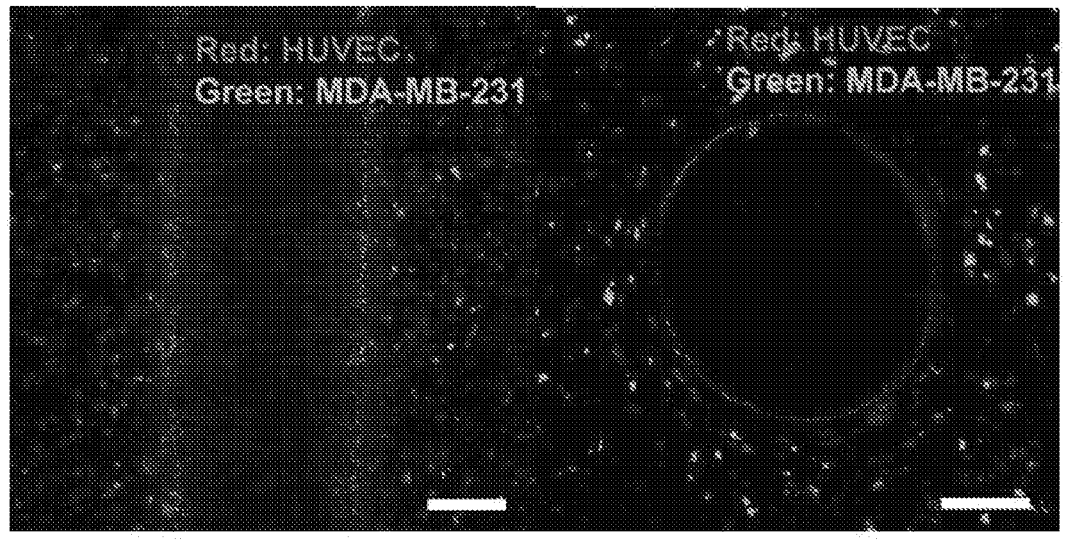
Figure 11C:
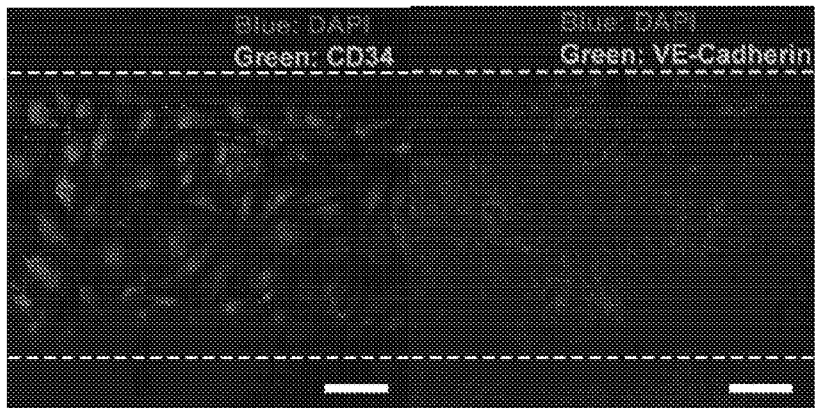
Figure 11D:
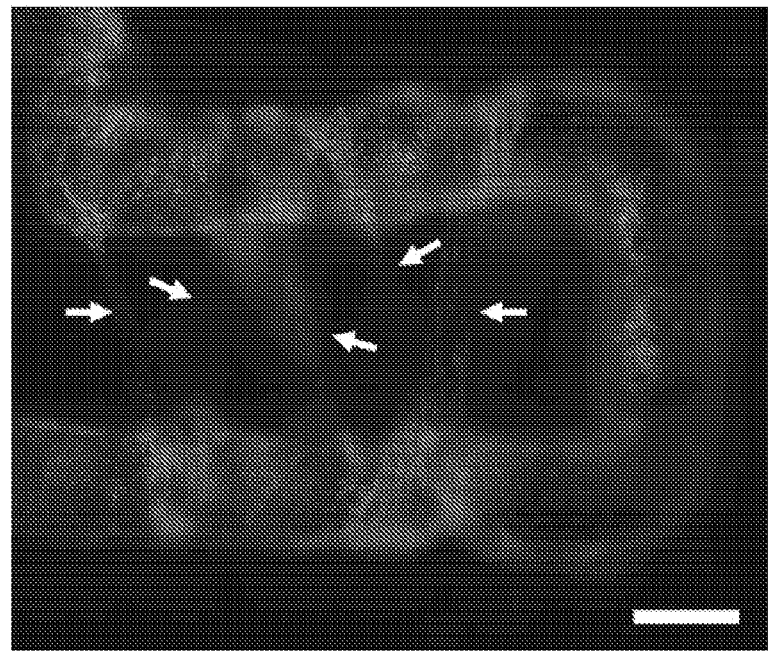

Following evacuation, the result is a hollow lumen within a gelated matrix body. This lumen can be directly perfused with media over time. Alternatively, the lumen can first be coated with endothelial or epithelial cells of a specific type in order to mimic a desired organ or tissue. Examples of lumens coated with human umbilical vein endothelial cells are shown in FIGS. 11A, 11B, 11D, 12, and 13. Examples of lumens coated with Caco-2 gut epithelial cells are shown in FIG. 16A. Immunostaining following coating and perfusion has demonstrated that endothelial cells maintain lineage and functional markers, shown in FIG. 11C, and Caco-2 gut epithelial cells exhibit in vivo morphologies and transporters, shown in FIG. 16B. FIG. 11D depicts an example of multi-channel structure produced via evacuation of a free-standing sinusoid-shaped PVA scaffold threaded with poly-vinyl alcohol-based threads (Solvron), and seeded with mCherry-labeled human umbilical vein endothelial cells. Scale bar represents 1 mm.

When multiple free-standing scaffolds are simultaneously encapsulated and evacuated from within a single matrix, it is possible to generate multiple lumens that can be coated with different types of cells to create hybrid cell systems. A schematic outlining this procedure is shown in FIG. 17A. An example of such a system, comprising a single channel of Caco-2 gut epithelial cells surrounded by a spiral channel of human umbilical vein endothelial cells, is shown in FIG. 17B.

In one embodiment, the interior lumen of the matrix construct is coated with endothelial cells from a human cell line following evacuation.

In one embodiment, the interior lumen of the matrix construct is coated with endothelial cells from a primary human source following evacuation. Examples include, but are not limited to, human umbilical vein endothelial cells, human microvascular endothelial cells, and human aortic endothelial cells.

In one embodiment, the interior lumen of the matrix construct is coated with epithelial cells from a human cell line following evacuation.

In one embodiment, the interior lumen of the matrix construct is coated with epithelial cells from a primary human source following evacuation. Examples include, but are not limited to, human bronchial epithelial cells, human small airway epithelial cells, and human intestinal epithelial cells.

Alternative embodiments can involve coating the interior lumen with other types of human primary cells, cell lines, or animal cells, or coating multiple lumens with different types of cells.

Embodiments containing endothelial cells can have the range of perfusion enhanced via induction of angiogenic sprouting either via matrix composition or the addition of angiogenic biomolecules. An example of a matrix contain-ing an endothelial-seeded lumen that has experienced angio-genic sprouting in shown in FIG. 14.

In addition, the lumen can be perfused with media con-taining additional growth factors or chemicals. Examples include, but are not limited to, sphingosine-1-phosphate, vascular endothelial growth factor, basic fibroblast growth factor, and phorbol-12-myristate-13-acetate.

Examples

Methodology of Construct Formulation Using Matrigel and Fibrin from an Evacuable Free-Standing PVA Structure with Post-Evacuation Seeding of Endothelial Cells Free-standing PVA structures are generated using a 3D printer, specifically, the Ultimaker³. The structures are sub-sequently placed within an enclosed holder comprising a glass slide bottom with walls composed of PDMS (Sylgard SE1700, Dow Corning Toray). Liquid-phase extracellular matrix formulations are produced by mixing matrigel, fibrinogen, transglutaminase, and thrombin in a cell-solution containing human mesenchymal stem cells (hMSCs), human umbilical vein endothelial cells (HUVECs), and invasive triple-negative breast cancer epithelial cells (MDA-MB-231). The final concentrations in the solution are 5 mg/mL matrigel and 10 mg/mL fibrinogen. The solution is subse-quently poured over the free-standing structure and allowed to polymerize at about 37° C. over about a 2-hour period. During this time, the PVA structures are dissolved by the aqueous media present within the matrix. Subsequently, the holder is attached to a peristaltic pump and the PVA scaffold is evacuated over 10-15 minutes using warm growth media. The structure is then perfused with cell growth media overnight. After 24 hours, a cell-suspension of HUVECs at a concentration of $5×10^6$ cells/mL is injected via pipette into the channel, and are allowed to incubate over 12 hours, forming a monolayer on the channel interior. The construct is then perfused over 30 days, allowing encapsulated cells to grow. An example of a structure generated from a spiral-shaped PVA scaffold and endothelialized with mCherry-labeled HUVECs is shown in FIG. 11A. An example of a structure generated from a sinusoidal PVA scaffold with a matrix containing GFP-labeled MDA-MB-231 cells and endothelialized with mCherry-labeled HUVECs is shown in FIG. 13.

Methodology of Construct Formulation Using Gelatin, Matrigel, and Fibrin from an Evacuable Free-Standing PVA Structure Threaded with PVA-Based Threads, with Post-Evacuation Seeding of Endothelial Cells Free-standing PVA structures are generated using a 3D printer, specifically, the Ultimaker³. The structures are sub-sequently placed within an enclosed holder consisting of a glass slide bottom with walls composed of PDMS (Sylgard SE1700, Dow Corning Toray). Liquid-phase extracellular matrix formulations are produced by mixing gelatin, matri-gel, fibrinogen, transglutaminase, and thrombin in a cell-solution containing human mesenchymal stem cells (hMSCs), human umbilical vein endothelial cells (HU-VECs), and invasive triple-negative breast cancer epithelial cells (MDA-MB-231). The final concentrations in the solu-tion are 15 mg/mL gelatin, 4 mg/mL matrigel and 10 mg/mL fibrinogen. The solution is subsequently poured over the free-standing structure and allowed to polymerize at 37° C. over a 2-hour period. During this time, the PVA structures are dissolved by the aqueous media present within the matrix. Subsequently, the holder is attached to a peristaltic pump and the PVA scaffold and PVA threads are evacuated over 10-15 minutes using warm growth media. The structure is then perfused with cell growth media overnight. After 24 hours, a cell-suspension of HUVECs at a concentration of $5 \times 10^6$ cells/mL is injected via pipette into the multi-channel network, and are allowed to incubate over 12 hours, forming a monolayer on the channel network interior. The construct is then perfused over 30 days, allowing encapsulated cells to grow. An example of a structure generated from a sinusoid-shaped PVA scaffold threaded with PVA-based threads and endothelialized with mCherry-labeled HUVECs is shown in FIG. 11C.

Methodology of Construct Formulation Using Matrigel and Fibrin from an Evacuable Free-Standing Alginate/Pluronics F127 Structure with Post-Evacuation Seeding of Endothelial Cells A blend of about 0.5% alginate and about 40% Pluronics F127 is formed by slowly dissolving lyophilized forms of both materials in water. Subsequently, free-standing blended structures of about 0.5% alginate and about 40% Pluronics F127 are generated using an extrusion-based 3D printer, and stabilized via crosslinking in 20 mM CaCl$_2$) solution. Pre-gelated extracellular matrix formulations are produced by mixing matrigel, fibrinogen, and thrombin in a cell-solution containing human mesenchymal stem cells (hMSCs), human umbilical vein endothelial cells (HUVECs), and invasive triple-negative breast cancer epithelial cells (MDA-MB-231). The final concentrations in the solution are 5 mg/mL matrigel and 10 mg/mL fibrinogen. The solution is subsequently poured into an enclosed holder comprising a glass slide bottom with walls composed of PDMS (Sylgard SE1700, Dow Corning Toray) to form a base layer on which the free-standing structure can be placed. The base layer is allowed to gelate for approximately 30 minutes before the free-standing alginate/Pluronics F127 vascular structure is placed on it. Subsequently, additional extracellular matrix solution is poured over the free-standing structure and allowed to polymerize at about 37° C. over an approximately 1-hour period. The gelated matrix is then placed at about 4° C. for about 30 minutes, allowing the Pluronics F127 to liquify, before being attached to a peristaltic pump and evacuated over about 10-15 minutes using an aqueous solution of about 20 mM EDTA. The structure is then perfused with cell growth media overnight. After about 24 hours, a cell-suspension of HUVECs at a concentration of $5 \times 10^6$ million is injected via pipette into the channel, and are allowed to incubate over about 12 hours, forming a mono-layer on the channel interior. The construct is then perfused over about 30 days, allowing encapsulated cells to grow. An example of an endothelialized structure generated from a sinusoidal structure of about 0.5% alginate and about 40% Pluronics F127 is shown in FIG. 12.

Methodology of Construct Formulation from Gelatin, Matrigel, and Fibrin Using an Evacuable Free-Standing Pattern Woven from PVA-Thread with Post-Evacuation Seeding of Intestinal Epithelial Cells Solvron threads are twisted and woven together to form a single thick pattern. The patterns are subsequently placed within an enclosed holder comprising a glass slide bottom with walls composed of PDMS (Sylgard SE1700, Dow Corning Toray). Specifically, ends of the thread are threaded within the inlet and outlet of the holder to stabilize the pattern. Liquid-phase extracellular matrix formulations are produced by first mixing gelatin, fibrinogen, and transglutaminase in a cell-solution containing human mesenchymal stem cells (hMSCs) and human intestinal epithelial cells (Caco-2) at about 37° C., then mixing Matrigel and thrombin separately at about 4° C. The separation of mixtures is necessary due to the opposite temperature-dependent gelation behavior of gelatin and matrigel. The two separate mixtures are finally blended such that the final concentrations in the solution are about 15 mg/mL gelatin, about 4 mg/mL matrigel and about 10 mg/mL fibrinogen. The solution is subsequently poured over the free-standing structure and allowed to polymerize at about 37° C. over about a 2-hour period. During this time, the PVA threads are dissolved by the aqueous media present within the matrix. Subsequently, the holder is attached to a peristaltic pump and the PVA scaffold is evacuated over about 10-15 minutes using warm growth media. The structure is then perfused with cell growth media overnight. After about 24 hours, a cell-suspension of Caco-2 cells at a concentration of about $5 \times 10^6$ cells/mL is injected via pipette into the channel, and are allowed to incubate over about 12 hours, forming a monolayer on the channel interior. The construct is then perfused over about 30 days, allowing encapsulated cells to grow.

Methodology of Construct Formulation Using Gelatin, Matrigel, and Fibrin from an Evacuable Free-Standing PVA Structure with MDA-MB-231 Cells in the Stroma, Post-Evacuation Seeding of Endothelial Cells, and Long-Term Perfusion to Generate a Tumor Organoid Free-standing PVA structures are generated using a 3D printer, specifically, the Ultimaker$^3$. The structures are subsequently placed within an enclosed holder comprising a glass slide bottom with walls composed of PDMS (Sylgard SE1700, Dow Corning Toray). Liquid-phase extracellular matrix formulations are produced by mixing matrigel, fibrinogen, transglutaminase, and thrombin in a cell-solution containing human mesenchymal stem cells (hMSCs), human umbilical vein endothelial cells (HUVECs), and invasive triple-negative breast cancer epithelial cells (MDA-MB-231). The final concentrations in the solution are about 15 mg/mL gelatin, about 4.0 mg/mL matrigel and about 10 mg/mL fibrinogen. The solution is subsequently poured over the free-standing structure and allowed to polymerize at about 37° C. over about a 2-hour period. During this time, the PVA structures are dissolved by the aqueous media present within the matrix. Subsequently, the holder is attached to a peristaltic pump and the PVA scaffold is evacuated over about 10-15 minutes using warm growth media. The structure is then perfused with cell growth media overnight. After about 24 hours, a cell-suspension of HUVECs at a concentration of about $5 \times 10^6$ cells/mL is injected via pipette into the channel, and are allowed to incubate over about 12 hours, forming a monolayer on the channel interior. The construct is then perfused over about 30 days, allowing encapsulated cells to grow. An example of tumor organoid-like structures generated via this methodology is shown in FIG. 15.

Methodology of Construct Formulation from Gelatin, Matrigel, and Fibrin with Embedded Tumor Fragments Using an Evacuable Free-Standing PVA Vascular Structure with Post-Evacuation Seeding of Endothelial Cells Independently of construct formulation, tumors via injection of MDA-MB-231 breast carcinoma cells into mice either subcutaneously or in the mammary gland. Tumors can be allowed to grow for a period of 1-3 months. Following deposition of the base layer (described below), tumors are excised and cut into small fragments in preparation for embedding.

Free-standing PVA structures are generated using a 3D printer, specifically, the Ultimaker$^3$. The structures are subsequently placed within an enclosed holder comprising a glass slide bottom with walls composed of PDMS (Sylgard SE1700, Dow Corning Toray). Liquid-phase extracellular matrix formulations are produced by first mixing gelatin, fibrinogen, and transglutaminase in a cell-solution containing human mesenchymal stem cells (hMSCs) and human umbilical vein endothelial cells (HUVECs) at about 37° C., then mixing Matrigel and thrombin separately at 4° C. The separation of mixtures is necessary due to the opposite temperature-dependent gelation behavior of gelatin and matrigel. The two separate mixtures are finally blended such that the final concentrations in the solution are about 15 mg/mL gelatin, about 4 mg/mL matrigel and about 10 mg/mL fibrinogen. The solution is subsequently poured to form a base layer beneath the free-standing PVA structure and allowed to polymerize at about 37° C. over about a 30-minute period.

During this time, tumor fragments are prepared (described above), and are placed on the deposited base layer. Subsequently, additional extracellular matrix solution is poured over the free-standing structure and tumor fragments and allowed to polymerize at about 37° C. over about a 1.5-hour period. During this time, the PVA structures are dissolved by the aqueous media present within the matrix. Subsequently, the holder is attached to a peristaltic pump and the PVA scaffold is evacuated over about 10-15 minutes using warm growth media. The structure is then perfused with cell growth media overnight. After about 24 hours, a cell-suspension of HUVECs at a concentration of about $5 \times 10^6$ cells/mL is injected via pipette into the channel, and are allowed to incubate over about 12 hours, forming a mono-layer on the channel interior. The construct is then perfused over about 30 days, allowing encapsulated cells to grow. An example of an endothelialized structure containing tumor fragments in about 15 mg/mL gelatin, about 4.0 mg/mL Matrigel, and about 10 mg/mL fibrin matrix is shown in FIG. 9, with accompanying data in FIG. 10.

Methodology of Construct Formulation Using Matrigel and Fibrin with Multiple Independent Lumens Generated from Evacuable Free-Standing PVA Structures with Post-Evacuation Seeding of Intestinal Epithelial Cells in One Lumen and Endothelial Cells in the Other.

Free-standing PVA structures are generated using a 3D printer, specifically, the Ultimaker$^3$. The structures are subsequently placed within an enclosed holder comprising a glass slide bottom with walls composed of PDMS (Sylgard SE1700, Dow Corning Toray). Patterns should be generated and structure should be placed such that there is no overlap or contact between them. For example, the placement of a linear construct within the interior of a spiral construct (FIG. 2B) will be described henceforth. Liquid-phase extracellular matrix formulations are produced by mixing matrigel, fibrinogen, transglutaminase, and thrombin in a cell-solution containing human mesenchymal stem cells (hMSCs), human umbilical vein endothelial cells (HUVECs), and human gut epithelial cells (Caco-2). The final concentrations in the solution are about 5 mg/mL matrigel and about 10 mg/mL fibrinogen. The solution is subsequently poured over the free-standing structures and allowed to polymerize at about 37° C. over a 2-hour period. During this time, the PVA structures are dissolved by the aqueous media present within the matrix.

Subsequently, the holder is attached to a peristaltic pump such that separate fluid lines connect to each distinct evacuable structure. The PVA scaffolds are evacuated over about 10-15 minutes using warm growth media to generate distinct lumens. The outer spiral lumen is perfused with EGM2 (Lonza), and the inner linear lumen is perfused using EMEM supplemented with about 20% FBS. After about 24 hours, a cell-suspension of HUVECs at a concentration of about $5 \times 10^6$ cells/mL is injected via pipette into the outer spiral channel, while a cell-suspension of Caco-2s at a concentration of about $5 \times 10^6$ cells/mL is injected via pipette into the inner linear channel. Both are allowed to incubate over 12 hours, forming distinct monolayers on the channel interior. The construct is then perfused over about 30 days, allowing encapsulated cells to grow. An example of a dual-lumen structure generated via evacuation of PVA from a about 15 mg/mL gelatin, about 4.0 mg/mL Matrigel, and about 10 mg/mL fibrin matrix, and seeded with both endothelial cells and Caco-2 gut epithelial cells is shown in FIG. 17B.

Variants of the claimed methods and techniques have been achieved using inks composed of materials such as Pluronics F127, gelatin, and carbohydrate glass, with matrices composed of various biocompatible materials, including gelatin, fibrin, collagen, and alginate. However, their use in generating vascular geometries more complex than 2D patterns or simple 3D grids has not been well-explored. In addition, because of their material properties, most fugitive inks are compatible with only a small selection of matrix materials. For instance, Pluronics F127 solutions liquify at low temperatures, making them difficult to use with materials such as collagen and Matrigel that require such temperatures when casting. Similarly, gelatin inks are incompatible with transglutaminase, a cross-linking enzyme commonly used to generate scaffolds from materials including collagen, gelatin, hyaluronic acid, and albumin.

As shown in FIG. 18A, the Schematic—PVA Chemistry outlines the chemistry associated with poly(vinyl alcohol) that allows for it to be easily dissolved in water.

As shown in FIG. 18B, in the first series of studies the viability of using PVA as a sacrificial vascular scaffold was assessed. PVA was confirmed to completely dissolve in media within a 1-hour time-frame, likely attributed to its water-soluble chemistry Depicted in FIG. 18C, the image "Prototype—Print-15gel-4mat-Tumors_top_02418" shows a completed tissue construct designed to sustain embedded MDA-MB-231 tumor fragments (excised from mice) over time.

As illustrated in FIG. 18D, the image, "Experimental Data—Dye_Perfusion_bottom_012308.png" shows an example of nutrient diffusion through the vascularized tissue construct via permeation patterns of dye over an 18 hour period.

As shown in FIG. 19A and FIG. 19B, an identical experiment was conducted with hMSCs to assess the effect on the stromal cells, with the duration increased to 20 days to account for a slower rate of growth. Both quantitative and qualitative results mirrored those of the breast cancer epithelial cells.

Figure 20A:
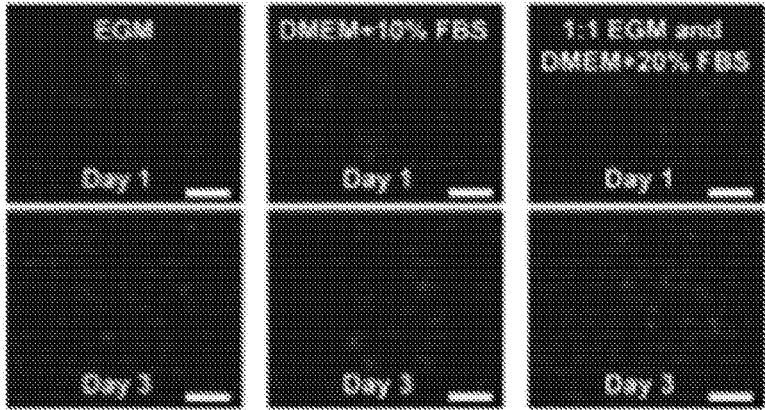
Figure 20B:
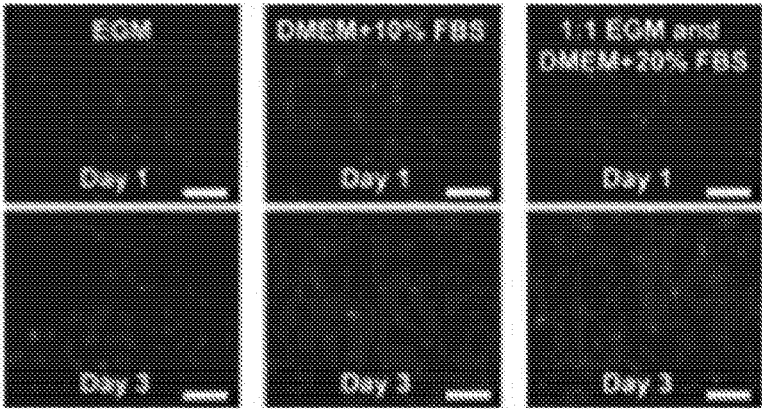
Figure 20C:
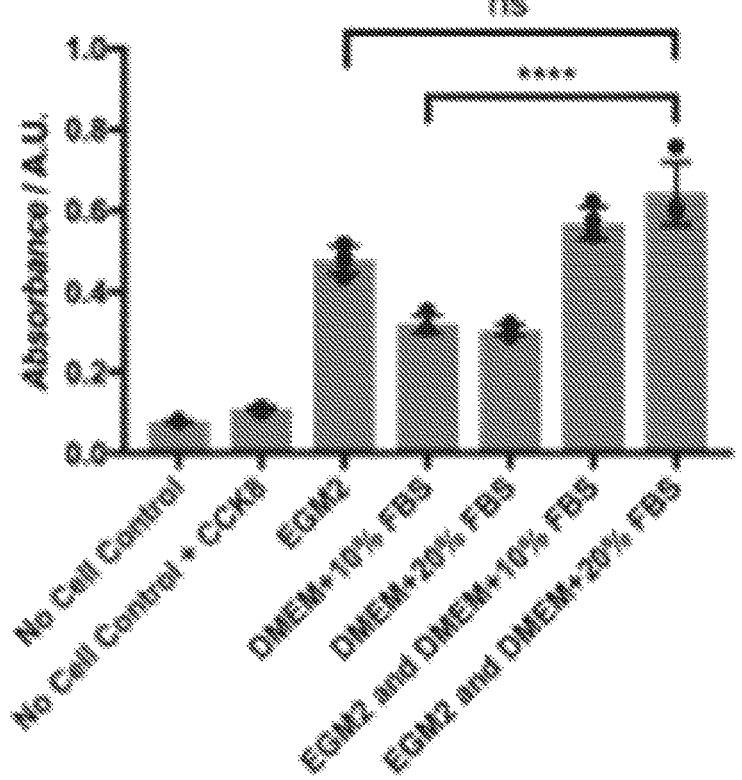
Figure 20D:
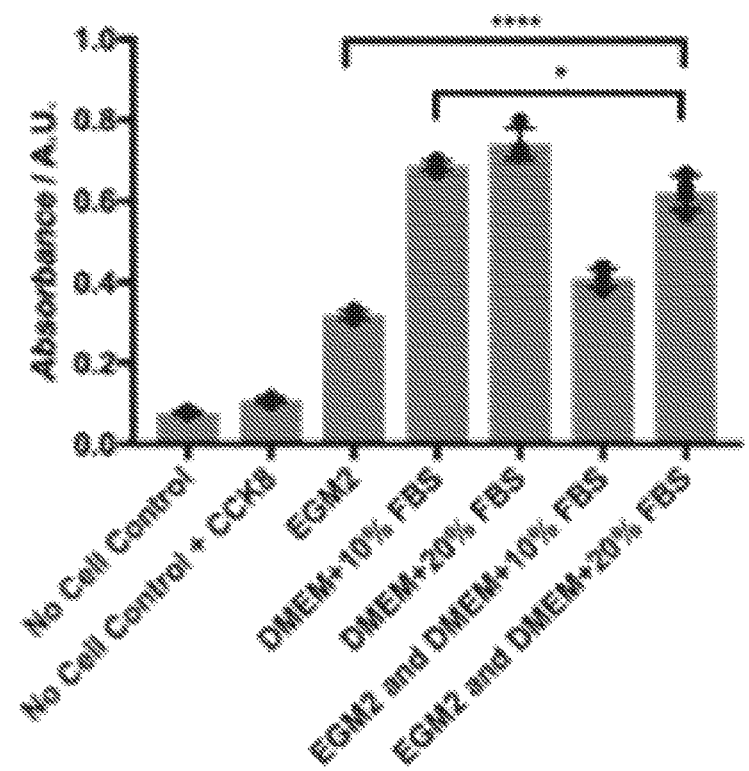

As depicted in FIG. 20A and FIG. 20B, with scale bars: 250 μm, fluorescent images showing optimization of media compositions for coculture of HUVECs and MDA-MB-231 cells. HUVEC and MDA-MB-231 cell growth in controls of EGM2 and DMEM supplemented with 10% FBS and 2 mM L-glutamine is compared with growth in the optimal formulation. In FIGS. 20C and 20D, with scale bars: 250 μm, quantitative confirmation of the results from previous figures (n=4 with P-values *P<0.05 and ****P<0.0001). Absorbance from the CCK8 assay shows relative growth in different media formulations, with overall results indicating that a 1:1 mixture of EGM2 and DMEM supplemented with 20% FBS and 4 mM L-glutamine allows for optimal HUVEC growth while minimally compromising MDA-MB-231 growth. Notably, all DMEM is supplemented with either 10% FBS and 2 mM L-glutamine, or 20% FBS and 4 mM L-glutamine.

Vascular Permeability Measurements: FITC-labeled 70 kDa dextran was flowed through channels either with or without a coating of HUVECs at a rate of 20 µL/min, and allowed to diffuse over 3 minutes to obtain an initial fluorescence measure. This rate was then reduced to 5 µL/min for the next 30 minutes, with fluorescent images taken every 5 minutes. Permeability was calculated in accordance with Equation (1), shown immediately below.

$$P = \frac{1}{I_i - I_b}\left(\frac{I_f - I_i}{t_f - t_i}\right)\frac{d}{4} \qquad (1)$$

Here, $I_b$ represents the mean background fluorescence present prior to the addition of dextran, $I_i$ and $I_f$ represent the mean fluorescence at initial and final timepoints, and d represents the diameter of the channel. All image processing was performed using ImageJ.

Atomic force microscopy (AFM) measurements: Hydrogel stiffness was measured by AFM as described. Nanoindentations were performed using a pyrex-nitride probe with a pyramid tip (spring constant~0.04 N/m, 35° half-angle opening, NanoAndMore USA Corporation, cat #PNP-TR) connected to a MFP-3D Bio Atomic Force Microscope (Oxford Instruments) mounted on a Ti—U fluorescent inverted microscope (Nikon Instruments). After calibration using a glass slide, samples were loaded on the AFM, submersed in phosphate buffered saline (PBS), and indented at a velocity of 2 µm/s with a trigger force of 2 nN. To ensure reproducibility, 3 force maps of ~20 force measurements were performed over a 90 µm×90 µm region per gel. In addition, measurements were made for three separate gels per condition. Elastic modulus was calculated based on a Hertz-based fit using a built-in code written in the Igor 6.34A software.

Cellularized Ex Vivo Tissue Construct

A cellularized ex vivo tissue construct is also provided herein. The cellularized ex vivo tissue construct may include a synthetic cell matrix having a plurality of viable cells or tissue fragments and a hydrogel, wherein the hydrogel comprises at least one lumen created by loading a free standing evacuable filament structure in the hydrogel while the hydrogel is in a liquid phase and dissolving and removing the free standing filament structure from the hydrogel after the hydrogel is gelated to a solid phase. In some embodiments of the construct, the free-standing evacuable filament structure can be poly-vinyl alcohol and three-dimensionally printed, stable in air, and dissolvable in an aqueous solvent. The structure further can include single-way channels in a three-dimensional structure selected from helical, sinusoidal, and linear channel. The structure also can be made of multi-way channels in a three-dimensional structure selected from cubical, grid, or a spherical channel. In some embodiments, the construct uses polyvinyl-alcohol structures of any general singular multi-channel configuration capable of being printed by a 3D printer. In some embodiments, two or more poly-vinyl alcohol structures can be used within the same construct.

The composite and/or solution around the freestanding evacuable filament structure can be deposited via micropipette to form a vascular pattern interpenetrating the one or more tissue patterns. The polyvinyl alcohol can be removed by partial solvation within the encapsulating matrix, followed by attaching the tissue construct to a peristaltic pump and perfusing for about 10-20 minutes. The polyvinyl alcohol can be removed by partial solvation within the encapsulating matrix, followed by manual perfusion using a pipette. In other embodiments, the polyvinyl alcohol can be removed by complete solvation within the encapsulating matrix, and gradual removal via bathing and incubation in aqueous media. Any form of cell growth media can be used as the solvent to remove the polyvinyl alcohol.

The three-dimensionally printed free-standing structure may be made of an alginate and pluronic blend, wherein the composite material is dissolvable in an EDTA solvent. The composite material can also be cross-linked via submersion in a calcium chloride solution at a concentration between 5-250 mM immediately following extrusion. A base matrix layer can also be deposited on a substrate before inserting the alginate-pluronic vasculature structure, wherein a top layer of matrix is poured over the vasculature structure to ensure that the evacuable filament is embedded between two matrix layers. The alginate-pluronic structures can be single-way channels comprising sinusoidal and linear channels. The alginate-pluronic structures can also be multi-way channels comprising cubical and grid-shaped channels. In some embodiments, the alginate-pluronic structures are any general singular multi-channel configuration capable of being generated by an extrusion printer.

The alginate-pluronic structure can be removed by incubation in about 2 degrees Celsius to about 8 degrees Celsius to liquify a Pluronics component, followed by evacuation with cold media containing EDTA by micropipettes. In some embodiments, threads constructed by poly-vinyl alcohol are knit into an evacuable, free-standing filament structure, wherein the material is stable in air and dissolvable in an aqueous solvent. In some embodiments of the construct, the polyvinyl alcohol can be removed by partial solvation within the encapsulating matrix, followed by attaching the tissue construct to a peristaltic pump and perfusing for 10-20 minutes. In other embodiments, the polyvinyl alcohol removal is done by partial solvation within the encapsulating matrix, followed by manual perfusion using a pipette. In further embodiments, polyvinyl alcohol removal includes complete solvation within the encapsulating matrix, and gradual removal via bathing and incubation in aqueous media. Any form of cell growth media can be used as the solvent to remove the polyvinyl alcohol. Any two or more of the included constructs can also be used in combination.

In some embodiments of the construct, the composite and/or hydrogel designed to mimic the extracellular matrix includes at least one of Matrigel, fibrin, gelatin, bovine collagen, porcine collagen, rat-tail collagen, gelatin methacrylate, alginate, decellularized extracellular matrix, or polyethylene glycol. In some embodiments, the combination of materials comprises about 1.5 mg/mL gelatin, about 4.0 mg/mL matrigel, and about 10 mg/mL fibrin. Moreover, one or more viable human or non-human cell types are encapsulated within the construct. Combinations of human and non-human cell types can also be encapsulated within the construct. The interior lumen or lumens of the construct can also be perfused with cell growth media. In certain embodiments, two or more distinct interior lumens of the construct can be perfused with distinct types of cell growth media.

One or more viable human or non-human endothelial or epithelial cell types can be used to coat the interior lumen of the construct following evacuation of the free-standing structure. In some embodiments, one or more different viable human or non-human endothelial or epithelial cell types are used in distinct lumens of the construct following evacuation of the free-standing structure. The cell growth medium or media used to perfuse the interior of the lumen or lumens of the construct can contain biological molecules or nanoparticles, including but not limited to growth factors, steroids, carbohydrates, cytotoxins, and amino acids. Extracellular matrix binding proteins, including but not limited to laminin and fibronectin, can be used to precoat the interior lumen of the construct following evacuation of the free-standing structure, but preceding the addition of endothelial or epithelial cell types. Fragments of excised tissue may also be encapsulated within the body of the matrix construct. In some embodiments, the construct is generated in replicate and treated with pharmacological agents.

EQUIVALENTS

While various illustrative embodiments of the invention are described above, it will be apparent to one skilled in the art that various changes and modifications may be made therein without departing from the invention.

REFERENCES

1. Kolesky, David B., Kimberly A. Homan, Mark A. Skylar-Scott, and Jennifer A. Lewis. "Three-Dimensional Bio-printing of Thick Vascularized Tissues." Proceedings of the National Academy of Sciences 113, no. 12 (Mar. 22, 2016): 3179-84. https://doi.org/10.1073/pnas.1521342113.
2. Lee, Vivian K., Diana Y. Kim, Haygan Ngo, Young Lee, Lan Seo, Seung-Schik Yoo, Peter A. Vincent, and Guohao Dai. "Creating Perfused Functional Vascular Channels Using 3D Bio-Printing Technology." Biomaterials 35, no. 28 (September 2014): 8092-8102. https://doi.org/10.1016/j.biomaterials.2014.05.083.
3. Miller, Jordan S., Kelly R. Stevens, Michael T. Yang, Brendon M. Baker, Duc-Huy T. Nguyen, Daniel M. Cohen, Esteban Toro, et al. "Rapid Casting of Patterned Vascular Networks for Perfusable Engineered Three-Dimensional Tissues." Nature Materials 11, no. 9 (September 2012): 768-74.
4. Laurent, Jérémie, Guillaume Blin, Francois Chatelain, Valérie Vanneaux, Alexandra Fuchs, Jérôme Larghero, and Manuel Théry. "Convergence of Microengineering and Cellular Self-Organization towards Functional Tissue Manufacturing." Nature Biomedical Engineering 1, no. 12 (December 2017): 939-56. https://doi.org/10.1038/s41551-017-0166-x.
5. Murphy, Sean V, and Anthony Atala. "3D Bioprinting of Tissues and Organs." Nature Biotechnology 32, no. 8 (August 2014): 773-85. https://doi.org/10.1038/nbt.2958.

What is claimed is:

1. A method of generating cellularized ex vivo tissue constructs, the method comprising:

suspending a plurality of viable cells and/or a plurality of tissue fragments in a liquid-phase hydrogel to prepare a composite and/or solution;

encapsulating a free-standing evacuable filament structure within the composite and/or solution;

gelating the composite and/or solution to mimic an extra-cellular matrix; and dissolving and evacuating the free-standing filament structure to create at least one lumen in the cellular matrix;

wherein:

the free-standing evacuable filament structure comprises a three-dimensionally printed free-standing structure;

the three-dimensionally printed free-standing structure comprises alginate and a pluronic blend;

the alginate and pluronic blend comprises about 10% to about 40% pluronic; and the composite is dissolvable in an EDTA solvent or an equivalent thereof.

2. The method of claim 1, further comprising cross-linking the composite via submersion in a calcium chloride solution at a concentration between about 5 to about 250 mM.

3. The method of claim 1, further comprising depositing a base matrix layer on a substrate before inserting the structure, wherein a top layer of matrix is poured over the structure to ensure that the evacuable filament is embedded between two matrix layers.

4. The method of claim 1, wherein the composite and/or solution designed to mimic the extracellular matrix comprises at least one of matrigel, fibrin, gelatin, bovine collagen, porcine collagen, rat-tail collagen, gelatin methacrylate, alginate, decellularized extracellular matrix, or polyethylene glycol.

5. The method of claim 4, wherein the composite and/or solution designed to mimic the extracellular matrix comprises any combination of at least one of matrigel, fibrin, gelatin, bovine collagen, porcine collagen, rat-tail collagen, gelatin methacrylate, alginate, decellularized extracellular matrix, or polyethylene glycol.

6. The method of claim 1, wherein at least one lumen of the construct is perfused with cell growth media and the extracellular matrix binding proteins laminin and fibronectin are used to precoat an interior lumen of the construct following evacuation of the free-standing structure, but preceding an addition of endothelial or epithelial cell types to coat the interior lumen.

7. The method of claim 1, further comprising generating an in vitro model of a tumor directly via encapsulation and perfused sustenance of primary tumor cells or a carcinoma cell line within the matrix.

8. The method of claim 1, further comprising generating an ex vivo model of a tumor and perfused sustenance of excised tumor fragments within the matrix.

9. The method of claim 1, further comprising generating an in vitro model of highly dense vasculature via seeding of human or animal endothelial cells within one or more lumens, encapsulation of human or animal endothelial cells within the matrix, and addition of pro-angiogenic biomolecules or a gradient of pro-angiogenic biomolecules.

10. The method of claim 1, further comprising generating an in vitro model of a gut via seeding and sustenance of primary intestinal epithelial cells or an intestinal epithelial cell line within one or more lumens.

11. The method of claim 1, further comprising generating any additional organoid models via seeding and sustenance of primary somatic cells, cell lines, or primary stem cells either within a lumen or within the matrix.

12. The method of claim 1, further comprising exposing endothelial or epithelial cells within the constructs to physiological flow rates or specific flow rates, wherein the physiological flow rates or the specific flow rates optionally are 0.01-100 mL/min.

13. The method of claim 1, further comprising three-dimensionally coculturing multiple cell types or excised tissue in an environment that mimics extracellular matrix.

14. The method of claim 1, further comprising generating organoid-like structures from excised tissue or primary stem cells in specific geometries.

15. The method of claim 1, wherein the alginate and pluronic blend comprises F127 pluronic.

* * * * *